United States Patent
Louvain et al.

(10) Patent No.: US 8,168,753 B2
(45) Date of Patent: May 1, 2012

(54) THROMBIN CLEAVABLE FACTOR X ANALOGUES

(75) Inventors: Virginie Louvain, Verrieres le Buisson (FR); Elsa Bianchini, Philadelphia, PA (US); Pierre-Emmanuel Marque, Paris (FR); Claire Calmel-Tareau, Paris (FR); Martine Aiach, Sevres (FR); Bernard Le Bonniec, Paris (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 1098 days.

(21) Appl. No.: 10/518,390

(22) PCT Filed: Jun. 30, 2003

(86) PCT No.: PCT/EP03/07793
§ 371 (c)(1),
(2), (4) Date: Oct. 25, 2005

(87) PCT Pub. No.: WO2004/005347
PCT Pub. Date: Jan. 15, 2004

(65) Prior Publication Data
US 2006/0148038 A1    Jul. 6, 2006

(30) Foreign Application Priority Data
Jul. 3, 2002  (FR) ...................... 02 08299

(51) Int. Cl.
*A61P 7/00* (2006.01)
*A61K 38/36* (2006.01)
*C12N 15/00* (2006.01)
*C12N 5/00* (2006.01)
*C07K 14/745* (2006.01)

(52) U.S. Cl. ...... 530/380; 530/384; 514/13.5; 514/14.4; 435/69.6; 435/69.1; 435/455

(58) Field of Classification Search .................. None
See application file for complete search history.

(56) References Cited

U.S. PATENT DOCUMENTS
6,357,386 B1 * 3/2002 Keller ..................... 118/723 VE
6,573,071 B1 * 6/2003 Himmelspach et al. ..... 435/69.6

FOREIGN PATENT DOCUMENTS
EP   768702 A1 * 4/1997
JP   63004615 A * 1/1988
WO   WO 9819965 A1 * 5/1998

OTHER PUBLICATIONS

Bianchini, Elsa P. et al. "Mapping of the Catalytic Groove Preferences of Factor Xa Reveals an Inadequate Selectivity for Its Macromolecule Substrates", The Journal of Biological Chemistry, vol. 277, No. 23, pp. 20527-20534, XP002235233 2002.

* cited by examiner

*Primary Examiner* — Marsha Tsay
(74) *Attorney, Agent, or Firm* — Oblon, Spivak, McClelland, Maier & Neustadt, L.L.P.

(57) ABSTRACT

The invention relates to factor X analogues containing the thrombin-cleavable sequence Pro-Arg-Ala in place of the sequence Thr-Arg-Ile of the activation site of native factor X. These factor X analogues can be used to obtain procoagulant medicinal products.

8 Claims, 4 Drawing Sheets

THROMBIN CLEAVABLE FACTOR X ANALOGUES

CROSS-REFERENCE TO RELATED APPLICATIONS

The present application is a National Stage (371) of PCT/EP03/07793, filed on Jun. 30, 2003, which claims priority to FR 0208299, filed on Jul. 3, 2002.

The present invention relates to thrombin-cleavable factor X derivatives, and to therapeutic uses thereof.

Blood clotting is the result of a cascade of enzyme reactions, the final step of which is the generation of thrombin, which induces the formation of a clot able to plug the vascular opening. Most of these reactions involve the proteolytic activation of inactive zymogens to active serine proteases.

This cascade of reactions is conventionally divided up into two pathways termed: "intrinsic pathway" and: "tissue factor pathway" or "extrinsic pathway".

The process of clotting via the intrinsic pathway is initiated by blood coming into contact with the subendothelial tissue. This contact leads to the activation of factor XII (FXII) to factor FXIIa, which then catalyses the activation of factor XI (FXI) to factor XIa (FXIa), which itself activates factor IX (FIX) to factor IXa. The latter binds to its cofactor, factor VIIIa (FVIIIa), to form the tenase complex. This complex cleaves factor X (FX) with great efficiency to produce activated factor X (FXa).

The process of clotting via the extrinsic pathway is initiated by tissue factor (TF), brought into contact with the blood when the formation of a vascular opening occurs. This tissue factor binds to activated factor VII (FVIIa) present in small amounts in the blood. The FVIIa-TF complex thus formed can activate factors IX and X.

The intrinsic pathway and the extrinsic pathway thus converge towards the activation of factor X to factor Xa, which constitutes one of the key enzymes in clotting.

Factor X is synthesized by hepatocytes in the form of a 448 amino acid precursor comprising, from the N-terminal end to the C-terminal end: a signal peptide, a propeptide, a "Gla" domain, two "EGF" (for Epidermal Growth Factor) domains of structure similar to that of epidermal growth factor, an activation peptide, and a catalytic domain of the serine protease type. The post-translational modifications of factor X are particularly complex: besides excision of the signal peptide and propeptide, they include carboxylation of the 11 glutamates of the "Gla" domain to γ-carboxyglutamates, excision of the tripeptide $Arg_{180}$-$Lys_{181}$-$Arg_{182}$ (the numbering refers to the product of translation of the factor X cDNA) separating the second EGF domain from the activation peptide, β-hydroxylation of the $Asp_{103}$ residue of EGF domain 1 to β-hydroxy aspartate, and at least five glycosylations, including four on the activation peptide.

The mature factor X circulating in the plasma therefore consists of two polypeptide chains linked by a disulphide bridge ($Cys_{172}$-$Cys_{342}$): the 139 amino acid "light" chain is composed of the Gla domain and the two EGFs; the 306 amino acid "heavy" chain is composed of the activation peptide joined to the catalytic domain.

The activation of factor X to a serine protease requires proteolytic cleavage between the activation peptide and the catalytic domain. The tenase complex, and also the FVIIa-TF complex, perform this cleavage between the $Arg_{234}$ and $Ile_{235}$ residues.

The activated factor X can also perform an auto-catalytic cleavage which slowly releases a small fragment at the C-terminal end of its heavy chain. Factors Xa α and β are thus distinguished according to whether or not this C-terminal peptide is present. The catalytic activity of these two forms of factor Xa is however identical (JESTY et al., J. Biol. Chem, 250, 4497-4504, 1975); consequently, and unless otherwise specified, in the explanation of the present invention, the term "factor Xa" denotes equally one or other of these two forms.

The binding of factor Xa with its cofactor, factor Va, forms the prothrombinase complex, which activates prothrombin to thrombin.

Thrombin is also an essential enzyme in clotting, and in haemostasis in general; it is a multifunctional serine protease. It induces platelet aggregation by cleaving its receptor at their surface, and converts circulating fibrinogen to an insoluble fibrin clot. This clot, by reinforcing the platelet thrombus already formed, blocks the vascular opening and thus makes it possible to stop the bleeding.

Thrombin can also activate factors V and VIII, which are respectively cofactors of the tenase and prothrombinase complexes, and also factor XI (FXI), which results in amplification of the reactions leading to its formation, in which these factors are involved.

FIG. 1 illustrates diagrammatically the main enzyme reactions of clotting via the extrinsic pathway or via the intrinsic pathway, and also the mechanism of auto-amplification of thrombin formation (represented by broken arrows).

A qualitative or quantitative deficiency in one of the factors involved in clotting leads to thrombotic or haemorrhagic manifestations which are often severe, and which can be life-threatening. In this context, mention will in particular be made of haemophilias A and B which result respectively from a deficiency in factor VIII or in factor Ix.

Haemophilias A and B are coagulopathies of the haemorrhagic type which are serious and quite common: the incidence thereof is approximately 1 case per 10 000 male births for haemophilia A and one case per 30 000 male births for haemophilia B.

In clinical terms, these two pathological conditions are indistinguishable: in both cases, it is the tenase complex resulting from the association of factor VIII with factor IX which is affected. As a result, there is insufficient production of activated factor X and, consequently, of thrombin.

This thrombin deficiency leads not only to a decrease in fibrin formation, but also to a decrease in the auto-amplification of thrombin production.

Treatments for haemophilia proposed at the current time are either replacement-type treatments aimed at reestablishing the function of the tenase complex, or treatments based on the use of one or more molecules which would make it possible to bypass this tenase complex (HEDNER, Thromb. Haemost., 82, 531-539, 1999).

The replacement treatment consists in administering the factor VIII or IX which is deficient. This is the only treatment available to date which makes it possible to correctly reestablish, besides the formation of fibrin, the auto-amplification of thrombin generation.

The main drawback of this treatment lies in the potential antigenicity of the molecule injected, which can be seen as foreign by the recipient's immune system. The development of neutralizing allo-antibodies directed against the factor used is a serious complication of replacement treatment, which makes it gradually ineffective.

Three approaches have been proposed for bypassing the tenase complex:

injection of mixtures of "vitamin K-dependent" clotting factors, comprising in particular prothrombin and factors VII, IX and X, factors VII and X being partially in the activated form. This treatment induces, however, rare but serious side effects: anaphylactic shocks and thrombotic accidents (myocardial infarction, disseminated intravascular coagulation), which can be explained by an action not localized to the vascular lesion. In addition, this treatment re-establishes auto-amplification of thrombin generation only in the case of type B haemophiliacs;

massive injection of activated factor VII which, in the presence of tissue factor, activates factor X independently of the tenase complex. Activated factor VII has the advantage that its action is located at the vascular opening where the complex with tissue factor forms. Its effectiveness in treating haemophilia might also be explained by a tissue factor-independent mechanism which uses the anionic phospholipids exposed by the activated platelets (HOFFMAN et al., Blood Coag. Fibrinolysis, 9 (suppl1), S61-65, 1998). The main drawbacks of using activated factor VII are its very short plasma half-life (less than three hours), which makes it necessary to administer it in large amounts, which makes the treatment very expensive. In addition, activated factor VII does not induce auto-amplification of thrombin generation. The amount of thrombin generated in a haemophiliac's plasma after the addition of a therapeutic dose of activated factor VII remains well below that generated in a normal plasma (BUTENAS et al., Blood, 99, 923-930, 2002);

administration of factor X, the activity of which is released only slowly in the plasma; in this context, three types of administration have been proposed: administration of activated factor X in combination with phospholipid vesicles (NI et al., Thromb. Haemost., 67, 264-271, 1992); administration of factor X which is activated but reversibly inhibited, for example by acetylation of the serine of the active site, and capable of re-activating slowly in the plasma by gradual deacylation (WOLF et al., Blood, 86, 4153-4157, 1995; LIN et al., Thromb. Res., 88, 365-372, 1997); administration of factor X in the form of a zymogen which can be activated in the plasma independently of the tenase complex. The latter approach uses factor X analogues in which the site for cleavage by the tenase complex is replaced with a site for cleavage by another protease.

HIMMELSPACH et al. (Thromb. Res., 97, 51-67 2000) thus describe factor X analogues in which the activation site is replaced with a cleavage site for furin. Once injected, this zymogen can slowly and continuously become converted to factor Xa.

PCT application WO 98/38317 proposes the construction of various factor X analogues in which the native activation site is replaced with a site for cleavage by another protease, chosen from factor XIa, thrombin, factor XIIa, kallikrein, factor Xa and furin. PCT application WO 01/10896 proposes replacement of the native site for activation by the tenase complex with a site for cleavage by factor XIa.

The main advantage of the use of factor X analogues lies in the plasma half-life of these analogues, which is similar to that of factor X (48 hours), and therefore much longer than that of activated factor X (less than 1 minute). The potential drawbacks of these analogues result from the difficulty in controlling their effects: the generation of activated factor X occurs continuously, without being regulated and without being localized at the vascular opening. In addition, these analogues do not make it possible to induce the amplification of thrombin generation.

It therefore appears to be desirable to have other factor X analogues which would not exhibit these drawbacks. With this aim, the inventors have sought thrombin-activatable factor X derivatives which would make it possible not only to bypass the deficient steps of the clotting cascade, and in particular the tenase complex, but also to reestablish auto-amplification of thrombin generation, according to the mechanism illustrated in FIG. 2. The activated form of this factor X derivative (FXa*) would in fact be capable (in combination with activated factor V) of forming a functional prothrombinase complex and therefore of activating prothrombin to thrombin. In return, the thrombin would activate further molecules of factor X derivative.

Physiologically, thrombin does not activate factor X. In fact, the efficiency of cleavage is conditioned by the nature of the amino acids framing the cleavage site, and in particular by the residues $P_3$-$P_2$-$P_1$-$P_1'$-$P_2'$-$P_3'$ of the activation site (the cleavage occurring between the residues $P_1$ and $P_1'$. Now, in the case of factor X, the sequence Leu-Thr-Arg-Ile-Val-Gly (LTR-IVG; SEQ ID NO:1) of the activation site is very dissimilar to the sequences Met-Pro-Arg-Ser-Phe-Arg (MPR-SFR; SEQ ID NO:2) or Val-Pro-Arg-Ser-Phe-Arg (VPR-SFR; SEQ ID NO:3) which are particularly favourable for cleavage by thrombin (MARQUE et al., J. Biol. Chem., 275, 809-816, 2000; BIANCHINI et al., J. Biol. Chem., 277, 20527-20534, 2002).

The residues $P_3$ to $P_1$ which precede the cleavage site are not involved in the catalytic activity of factor X after activation: they are part of the activation peptide which is released after cleavage. The same is not true for the residues $P_1'$ to $P_3'$, which immediately follow the cleavage site: as in all serine proteases, the N-terminal residues of the catalytic chain of activated factor X are involved in the enzymatic activity. The residue $P_1'$ in particular plays a fundamental role in the catalytic mechanism of the enzyme.

Substitution of the sequence LTR-IVG (SEQ ID NO: 1) of the activation site of factor X with the sequence VPR-SFR (SEQ ID NO: 3) would make it possible to multiply by $10^5$ the rate of cleavage of factor X by thrombin. However, there is a risk that this substitution would be prejudicial to the enzymatic activity of the factor Xa. It is not in fact possible to predict what the enzymatic activity of an activated factor X analogue in which the heavy chain begins with a residue other than isoleucine would be.

PCT application WO 98/38317 describes a factor X analogue in which the sequence LTR-IVG of the native activation site is replaced with the sequence Thr-Arg-Arg-Ser-Val-Gly (TRR-SVG; SEQ ID NO:4), and which is presented as being potentially thrombin-cleavable. However, no indication is given regarding the effective cleavage of this zymogen by thrombin, and even less regarding the catalytic activity of the factor Xa analogue which would result from this cleavage.

The inventors have tested various substitutions at positions $P_3$-$P_2$-$P_1$-$P_1'$-$P_2'$-$P_3'$ of the native activation site of factor X, in order to study the effects of these substitutions, firstly, on the cleavage by thrombin and, secondly, on the enzymatic activity of the factor Xa analogue which results therefrom.

They have thus noted that substitution, at positions $P_2$-$P_1$-$P_1'$, of the sequence TR-I with the sequence PR-A makes it possible to obtain factor X analogues which can be effectively cleaved by thrombin, and the cleavage of which generates a factor Xa analogue having a catalytic activity which, although decreased, is similar to that of its non-mutated homologue and compatible with a normal physiological function; in addition, this decrease in the catalytic activity is compensated by an increase in the half-life compared to that of the native factor Xa. This increase in the half-life results from better resistance to serpines (serine protease inhibitors in the plasma), and in particular to antithrombin.

Consequently, a subject of the present invention is a factor X analogue in which the sequence Thr-Arg-Ile of the activation site of native factor X is replaced with a thrombin-cleavable sequence, characterized in that said thrombin-cleavable sequence is the sequence Pro-Arg-Ala.

A subject of the present invention is also any factor Xa analogue which can be obtained by cleavage of a factor X analogue according to the invention, by thrombin.

The term "factor X analogue" here denotes both the mature factor X molecule and its intracellular precursor; the term "factor Xa analogue" denotes the molecule in the activated, α or β form.

As regards the substitutions at positions $P_3$, $P_2'$ and $P_3'$ of the activation site, they have less influence on the effectiveness of the cleavage by thrombin, and on the enzymatic activity of the factor Xa analogue obtained than those made at positions $P_2$, $P_1$ or $P_1'$.

Thus, at $P_3$, the Leu residue of native factor X can be conserved, or substituted with any amino acid, with the exception of Pro, Asp and Glu; at $P_2'$, the Val residue of native factor X can be conserved, or substituted with an amino acid preferably chosen from Ile, Leu and Phe; at $P_3'$, the Gly residue of native factor X can be conserved, or substituted with an amino acid preferably chosen from Asn and His.

Optionally, it is possible to combine the activation site modifications specific to the factor X analogues and factor Xa analogues in accordance with the invention with other modifications concerning different domains of factor X or of factor Xa and making it possible to improve some of their properties. Thus, it is possible, for example, to replace the propeptide of native factor X with that of prothrombin, in order to obtain a better yield of γ-carboxylated mature protein, as described by CAMIRE et al. (Biochemistry, 39, 14322-14329, 2000).

A subject of the present invention is also nucleic acid molecules encoding factor X analogues in accordance with the invention.

These nucleic acid molecules can be obtained by conventional methods well known to those skilled in the art, in particular by site-directed mutagenesis of a nucleic acid molecule encoding native factor X.

The present invention also encompasses the expression cassettes comprising a nucleic acid molecule in accordance with the invention associated with suitable elements for controlling transcription (in particular promoter and, optionally, terminator) and optionally translation, and also the recombinant vectors into which a nucleic acid molecule in accordance with the invention is inserted. These recombinant vectors may be, for example, cloning vectors, expression vectors, or gene transfer vectors which can be used in gene therapy.

A subject of the present invention is also prokaryotic or eukaryotic host cells genetically transformed with at least one nucleic acid molecule according to the invention. Preferably, for the expression and the production of the factor X analogues in accordance with the invention, eukaryotic cells, for example mammalian cells, will be chosen.

The construction of vectors in accordance with the invention and the transformation of the host cells can be carried out by conventional molecular biology techniques.

The present invention also encompasses animals, and in particular non-human transgenic mammals, harbouring at least one transgene comprising an expression cassette in accordance with the invention. These transgenic mammals can be used, for example, for producing factor X analogues in accordance with the invention, in a manner similar to that which has already been proposed for the production of other proteins of therapeutic interest (BRINK et al., Theriogenology, 53, 139-148 2000).

The factor X analogues in accordance with the invention can be obtained, for example, by culturing genetically transformed cells in accordance with the invention and recovering, from the culture, the analogue expressed by said cells. They can then, if necessary, be purified by conventional procedures, known in themselves to those skilled in the art, for example by fractionated precipitation, in particular precipitation with ammonium sulphate, electrophoresis, gel filtration, affinity chromatography, etc.

A subject of the present invention is also the use of factor X analogues or of factor Xa analogues in accordance with the invention, or of the nucleic acid molecules encoding these analogues, for obtaining procoagulant medicinal products.

Medicinal products obtained from factor X analogues or factor Xa analogues in accordance with the invention can be used in the context of the prevention or treatment of coagulopathies of the haemorrhagic type, ensuing in particular from a deficiency in factor VIII, IX or XI. These may in particular be haemophilia A or haemophilia B, which may or may not be complicated by the presence of inhibitors (neutralizing alloantibodies directed against factor VIII or IX conventionally used for the treatment); they may also be acquired haemophilias resulting from the appearance of autoantibodies associated with another pathological condition (autoimmune disease, cancer, lymphoproliferative syndrome, idiopathic disorder, etc.).

Nucleic acid molecules according to the invention can advantageously be incorporated into medicinal products which can be used in gene therapy. The vectors conventionally used in gene therapy, such as viral vectors (for example a vector of the adenovirus or retrovirus type), liposomes, etc., can be used to obtain medicinal products in accordance with the invention.

The factor Xa analogues in accordance with the invention have, outside the prothrombinase complex, a catalytic activity which is much weaker than that of native factor Xa. However, within the prothrombinase complex (i.e. under physiological conditions), the decrease in their activity compared to native factor Xa is much less, and they are effectively capable of correcting the effects of a depletion of factor VIII or IX. In addition, due to their considerable resistance to antithrombin, the factor Xa analogues in accordance with the invention have the advantage of having a longer half-life, which compensates for their weaker activity. Although it is much slower, there is still inhibition by antithrombin (which is proportional to the catalytic activity), which makes it possible to conserve a mechanism of autoregulation similar to that of native factor Xa.

In addition, the action of the factor Xa analogues in accordance with the invention remains localized at the vascular opening since, as shown in FIG. 2, the enzyme cascade in which these analogues are involved is triggered by tissue factor. Finally, as also shown in FIG. 2, the use of the factor X analogues in accordance with the invention makes it possible to re-establish the auto-amplification of thrombin generation.

The overall result of this is a therapeutic effect which is better targeted and easier to control than that of the factor X or factor Xa analogues of the prior art.

The factor X analogues in accordance with the invention can, for example, be used at plasma concentrations of the order of 0.1 to 0.5 μM, i.e. 5 to 25 mg/l. These concentrations can be obtained by administering doses which are close to those which are used in the case of treatments with factor VIIa, but less frequently.

The present invention will be understood more clearly from the further description which follows, which refers to non-limiting examples of preparation and of characterization of a factor X analogue in accordance with the invention.

BRIEF DESCRIPTION OF DRAWINGS

FIG. 2 also shows the use of the factor X analogues in accordance with the invention makes it possible to re-establish the auto-amplification of thrombin generation.

FIG. 4 compares the procoagulant effect of the GDX-AVG derivative (○) (not activated) with the GD-FX derivative (□) (not activated) in factor VIII-depleted (4A) or factor IX-depleted (4B) plasma.

EXAMPLE 1

Figure 1:
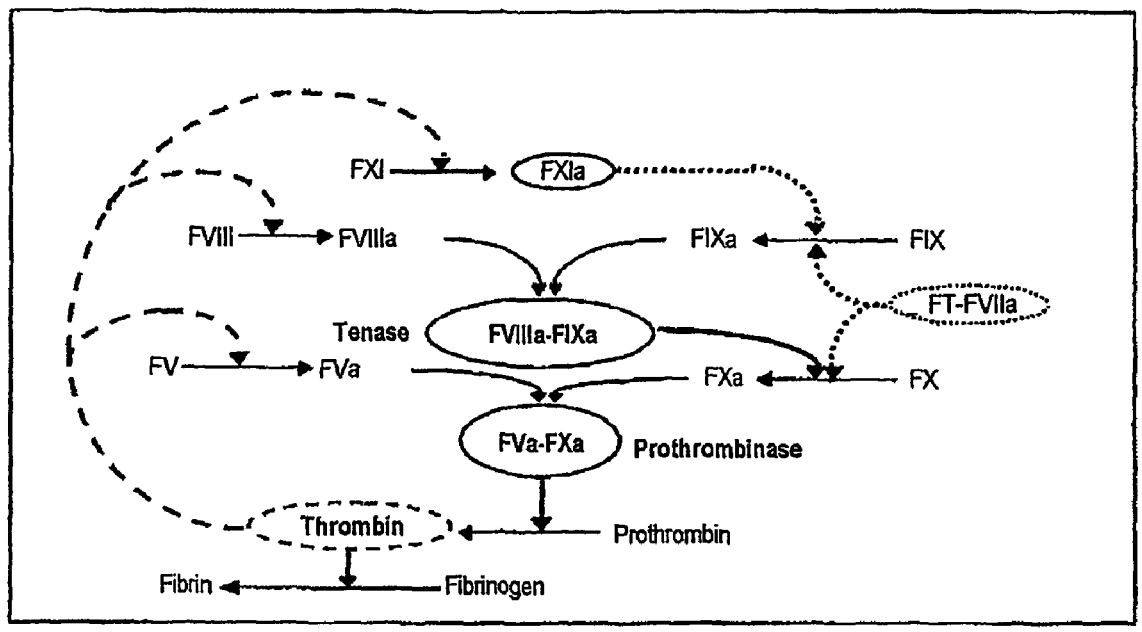
FIG. 1 illustrates diagrammatically the main enzyme reactions of clotting via the extrinsic pathway or via the intrinsic pathway, and also the mechanism of auto-amplification of thrombin formation (represented by broken arrows).
Figure 2:
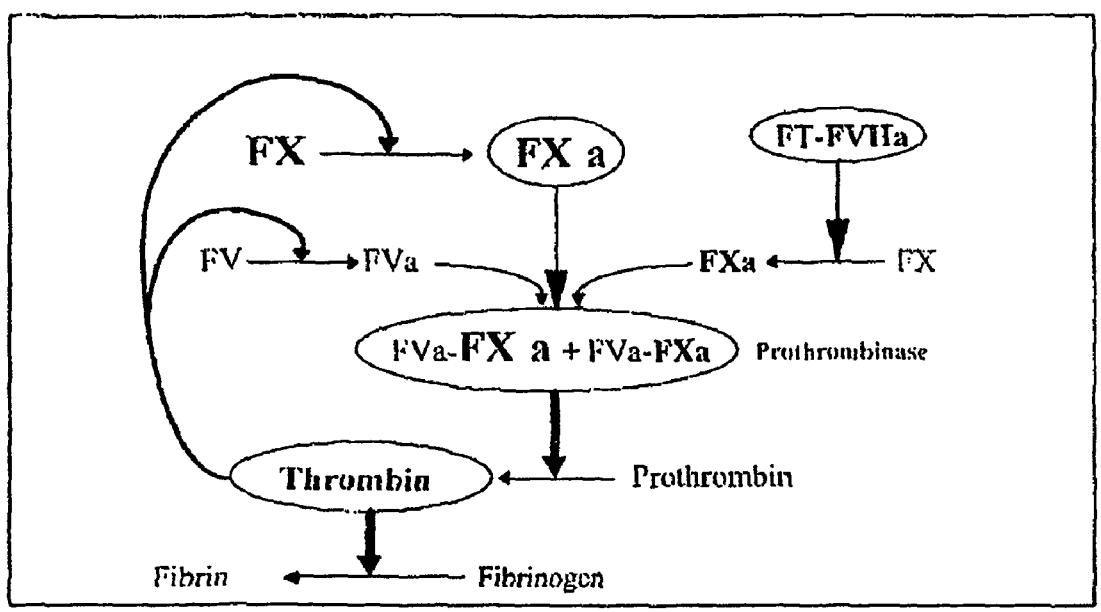
FIG. 2 illustrates the enzyme cascade in which the Factor Xa analogues of the invention are involved.

Construction of Expression Vectors for Factor X Analogues

Various human factor X derivatives were constructed:
a derivative, hereinafter referred to as "FX-recombinant", differing from native factor X only by the addition, at its C-terminal end, of an 11 amino acid peptide (EQKLISEEDLN; SEQ ID NO:5) which is recognized by the monoclonal antibody 9E10 (PHARMINGEN, San Jose, USA); this modification makes it possible to facilitate detection and purification of the expressed protein;
a derivative, hereinafter referred to as "GD-FX", which differs from the "recombinant" derivative in that it also lacks a Gla domain, which makes it possible to increase the amount of recombinant protein expressed, and in that it comprises, at its N-terminal end, a 12 amino acid sequence (EDQVDPRLIDGK; SEQ ID NO:6), constituting an epitope recognized by the monoclonal antibody HPC-4 (ROCHE DIAGNOSTIC, Meylan, France);
the derivatives, hereinafter referred to as GDX-IVG, GDX-IFG, GDX-AVG, GDX-IFR, GDX-SVG, GDX-SFR, which differ from the GD-FX derivative by the modification of one or more of the residues at positions $P_3$, $P_2$, $P_1$, $P_1'$, $P_2'$ or $P_3'$ of the activation site.

The residues $P_3$ to $P_3'$ of the activation site of normal factor X isolated from plasma (FX-plasma), and of each of the derivatives above, are indicated in Table I.

TABLE I

|  | $P_3$ | $P_2$ | $P_1$ | $P_1'$ | $P_2'$ | $P_3'$ |
|---|---|---|---|---|---|---|
| FX-plasma (SEQ ID NO:1) | Leu | Thr | Arg | Ile | Val | Gly |
| FX-recombinant (SEQ ID NO:1) | Leu | Thr | Arn | Ile | Val | Gly |
| GD-FX (SEQ ID NO:1) | Leu | Thr | Arg | Ile | Vat | Gly |
| GDX-IVG (SEQ ID NO:7) | Val | Pro | Arg | Ile | Val | Gly |
| GDX-IFG (SEQ ID NO:8) | Val | Pro | Arg | Ile | Phe | Gly |
| GDX-AVG (SEQ ID NO:9) | Val | Pro | Arg | Ala | Val | Gly |
| GDX-IFR (SEQ ID NO:10) | Val | Pro | Arg | Ile | Phe | Arg |
| GDX-SVG (SEQ ID NO:11) | Val | Pro | Arg | Ser | Val | Gly |
| GDX-SFR (SEQ ID NO:12) | Val | Pro | Arg | Ser | Phe | Arg |

The expression vectors used to construct these derivatives are obtained from the vector pNUT-hGH (PALMITER et al., Science, 1983, 222, 809-814, 1983) by replacement of the sequence encoding human growth hormone (hGH) with the sequence encoding the desired factor X derivative.

Construction of the Vector pNUT-FX

The vector referred to as "pNUT-FX" makes it possible to express the "FX-recombinant" derivative in eukaryotic cells.

The complete cDNA of human factor X used (1467 base pairs) was initially cloned by MESSIER et al. (Gene, 99, 291-294, 1991) into the SalI site of the plasmid pBluescript KS(−).

This cDNA was recovered by PCR amplification from the vector pBluescript containing it. The primers used are represented in Table II below. The melting temperature used (Th°) is indicated in the final column of the table.

TABLE II

| Primer | Sequences (5'→3') | Th (° C.) |
|---|---|---|
| 1 | ACGCGGATCCGCGATGGGGCGCCCACT GCA (SEQ ID NO: 13) | 51 |
| 2 | TCCCCCGGGGGATCAGTTCAGGTCTTCC TCGCTGATCAGCTTCTGCTCCTTTAAT GGAGAGGACGTTA (SEQ ID NO: 14) | 51 |

Primers 1 (SEQ ID NO:13) and 2 (SEQ ID NO:14) introduce respectively a BamHI restriction site positioned 5', and an XmaI site positioned 3', of the sequence encoding the factor X. Moreover, primer 2 introduces, just before the stop codon of the factor X cDNA, the sequence encoding the epitope recognized by the monoclonal antibody 9E10.

The amplification protocol is as follows: the amplification is carried out in a volume of 100 µl containing 2 µg (7 nM) of plasmid pBluescript, 2 µM of each of primers 1 and 2, 0.2 mM of each dNTP (dATP, dCTP, dGTP, dTTP; AMERSHAM PHARMACIA BIOTECH, Orsay, France) and 6 units of Pfu DNA polymerase (STRATAGENE) in the buffer recommended by the manufacturer. The amplification is carried out in a DNA THERMAL CYCLER (model 480, PERKIN ELMER, Roissy, France) according to the following programme: an initial denaturation of 5 minutes at 95° C., followed by 30 cycles each comprising 45 seconds of denaturation at 95° C., 45 seconds of hybridization at a temperature at least 4° C. below the melting temperature of the primers, and 3.5 minutes of elongation at 72° C. The amplification is terminated by incubation for 10 minutes at 72° C.

The amplification product is purified by phenol/chloroform extraction, and concentrated by precipitation with ethanol. The ends are then blunt-ended and phosphorylated by incubation for 30 minutes at 37° C. in the presence of 5 units of $T_4$ DNA polymerase (NEW ENGLAND BIOLABS, Beverly, Mass., USA), 10 units of $T_4$ polynucleotide kinase (NEW ENGLAND BIOLABS) and 0.3 mM of dNTP (AMERSHAM PHARMACIA BIOTECH). The fragment of interest is purified using the "QIAquick Gel Extraction Kit" (QIAGEN, Courtaboeuf, France), after separation on a standard 1% agarose gel, according to the manufacturer's instructions.

In parallel, 40 µg, in 140 µl (86 nM) of a recipient vector (pBluescript, STRATAGENE) are linearized with 400 units of EcoRV for 90 minutes at 37° C. The ends of the linearized pBluescript vector are dephosphorylated by incubation for 60 minutes at 37° C. in the presence of 50 units of calf intestine alkaline phosphatase (NEW ENGLAND BIOLABS); this vector is then purified as above, using the "QIAquick Gel Extraction Kit", after separation in standard 1% agarose.

The insert is introduced into the recipient vector by ligation, incubating 10 nM of vector with 20 nM of insert in the presence of 400 units of $T_4$ DNA ligase (NEW ENGLAND BIOLABS) for 24 hours at ambient temperature in 10 µl of the buffer recommended by the manufacturer.

The resulting plasmid (pBluescript-FX) is amplified in the *E. coli* strain DH5α (and purified according to standard protocols, described by SAMBROOK et al. (Molecular Cloning: A laboratory Manual. Cold Spring Harbor Laboratory Press, 1989).

The insert of the plasmid pBluescript-FX is transferred into the vector pNUT-hGH by cassette exchange, according to the following protocol:

Two µg (4 nM) of pNUT-hGH are digested with 60 units of BamHI for 2 hours at 37° C. in 100 µl of reaction mixture. The vector thus linearized is purified by phenol/chloroform extraction, followed by precipitation with ethanol. It is then taken up in 10 µl of 10 mM Tris, pH 8.0, containing 1 mM of EDTA, and digested with 30 units of XmaI for 3 hours at 37° C.

The two fragments derived from this second digestion are dephosphorylated by incubation for one hour at 37° C. in the presence of 150 units of alkaline phosphatase.

The linearized pNUT vector is separated from its former insert (containing the sequence encoding hGH) by electrophoresis in standard 1% agarose, and purified using the "QIAquick Gel Extraction Kit".

In parallel, 130 µg (1.3 µM) of pBluescript-FX are digested with 20 units of BamHI for 1 hour at 37° C. in 30 µl of reaction mixture. The linearized vector is purified by phenol/chloroform extraction followed by precipitation with ethanol. It is then taken up in 10 µl of 10 mM Tris, pH 8.0, containing 1 mM of EDTA, and digested with 30 units of XmaI for 3 hours at 37° C.

The FX insert is separated from its former vector by electrophoresis in standard 1% agarose, and purified using the "QIAquick Gel Extraction Kit".

The vector pNUT-FX is obtained by ligation of the FX insert into the vector pNUT in the presence of $T_4$ DNA ligase, as described above.

Construction of the Vector pNUT-GDX

The presence of a "Gla" domain considerably limits the synthesis of a recombinant protein in a eukaryotic cell. Its removal makes it possible to multiply five-fold the amount of recombinant protein expressed.

In addition, the "Gla" domain of factor X is necessary for its biological activity, but is not essential for the proteolytic activity with respect to substrates which interact only with the catalytic groove. The preparation of derivatives lacking "Gla" domain therefore makes it possible to rapidly determine the effect of modifications of the residues juxtaposing the activation site, on the serine protease activity.

The vector pNUT-ETW (LE BONNIEC et al., J. Biol. Chem., 267, 6970-6976, 1992) expresses a derivative of human prothrombin lacking its "Gla" domain, and fused, at the N-terminal, to the signal peptide of bovine factor V and to a 12 amino acid sequence (EDQVDPRLIDGK; SEQ ID NO: 6), constituting an epitope recognized by the monoclonal antibody HPC-4.

To construct the vector pNUT-GDX, the "signal peptide and "Gla" domain of the vector pNUT-FX" assembly was substituted with the "signal peptide, propeptide and HPC-4 epitope of the vector pNUT-ETW" assembly.

The primers used to amplify the fragments of the vectors pNUT-FX and pNUT-ETW are represented in Table III below. The PCR amplification is carried out as described above for the vector pNUT-FX.

TABLE III

| Primers | SEQUENCES (5'→3') | Th (° C.) |
|---|---|---|
| 3 | TATGCGTGGGCTGGAGCAACC (SEQ ID NO: 15) | 62 |
| 4 | TTATTAGGACAAGGCTGGTGGG (SEQ ID NO: 16) | 62 |
| 5 | CTTCCCATCAATGAGCCGCGG (SEQ ID NO: 17) | 62 |
| 6 | CCGCGGCTCATTGATGGGAAGGATGGCGACCAGTGTGAGACC (SEQ ID NO: 18) | 62 |

The amplification of the fragment derived from pNUT-ETW (which includes the BamHI and XmaI sites of pNUT, the sequence encoding the signal peptide of factor V and that encoding the epitope recognized by the antibody HPC-4) is carried out with primers 3 (SEQ ID NO:15) and 5 (SEQ ED NO:17); the amplification of the fragment derived from pNUT-FX (which includes the sequence encoding the two EGF domains, the activation peptide, and the serine protease domain of factor X, and also the epitope recognized by the antibody 9E10) is carried out with primers 6 (SEQ ID NO:18) and 4 (SEQ ID NO:16). Primers 5 and 6 are partially complementary (primer 6 introduces, positioned 5' of the first EGF, a portion of the sequence encoding the epitope recognized by the antibody HPC-4), which makes it possible to join up the fragments derived from the two PCRs by "Mega-primer" PCR(HO et al., Gene, 15, 51-59, 1989) in the presence of primers 3 and 4. The product of this PCR is digested with 40 units of XmaI (in a volume of 400 µl), and the restriction fragment (with an XmaI site at each end) is purified using the QLAquick Gel Extraction Kit after separation in a 1% agarose gel.

Furthermore, 6 µg, in 140 µl (12 nM), of vector pNUT-hGH are digested with 20 units of XmaI, for 2 hours at 37° C. The vector thus linearized is separated from its former insert (sequence encoding hGH) by electrophoresis in standard 1% agarose, and purified using the QIAquick Gel Extraction Kit. The vector without insert (0.1 µg in 10 µl, i.e. 2.7 nM) is recircularized by ligation in the presence of 400 units of $T_4$ DNA ligase for 16 hours at ambient temperature.

The recircularized pNUT vector is amplified in the *E. coli* strain DH5α and purified.

40 µg in 100 µl (i.e. 110 nM) of the vector pNUT without insert are linearized with 10 units of XmaI for 3 hours at 37°

C., and its ends are dephosphorylated by incubation for 1 hour at 37° C. in the presence of 150 units of alkaline phosphatase. The vector pNUT thus prepared is isolated using the QIAquick Gel Extraction Kit, after separation in a 1% agarose gel.

The vector pNUT-GDX is obtained by ligation of the fragment derived from the "Mega-primer" PCR into the vector pNUT in the presence of $T_4$ DNA ligase, as described above, and selection, on the basis of the BamHI, XmaI, PstI or EcoRI restriction profiles, of the constructs containing the insert in the correct orientation.

Site-Directed Mutagenesis of the Vector pNUT-GDX

In native factor X (and also in the GDX-FX derivative), the sequence of the residues $P_3$-$P_2$-$P_1$-$P_1'$-$P_2'$-$P_3'$ framing the cleavage site (the cleavage taking place between $P_1$ and $P_1'$) is LTR-IVG (SEQ ID NO: 1).

The six factor X analogues prepared: GDX-IVG, GDX-IFG, GDX-AVG, GDX-IFR, GDX-SVG, GDX-SFR have respectively the sequence $P_3$-$P_2$-$P_1$-$P_1'$-$P_2'$-$P_3'$: VPR-IVG (SEQ ID NO: 7), VPR-IFG (SEQ ID NO: 8), VPR-IFR (SEQ ID NO: 9), VPR-AVG (SEQ ID NO: EA, VPR-SVG (SEQ ID NO: 11) and VPR-SFR (SEQ ID NO: 12).

The vectors expressing these factor X analogues were prepared by mutagenesis of the vector pNUT-GDX by a method derived from that of JONES et al. (Nature, 344, 793-794, 1990).

The sequences of the primers used for the mutagenesis of the vector pNUT-GDX are indicated in Table IV (SEQ ID NO: 19 to SEQ ID NO:30).

The "sense" primer (s) hybridizes on the non-coding strand, and the "antisense" primer (a) hybridizes on the coding strand.

TABLE IV

| | |
|---|---|
| GDX-IVG (s) | AGGGGCGACAACAACGTGCCTAGGATCGTGGG CGGCCAGGAATGCAAG (SEQ ID NO: 19) |
| GDX-IVG (a) | CTTGCATTCCTGGCCGCCCACGATCCTAGGCA CGTTGTTGTCGCCCCT (SEQ ID NO: 20) |
| GDX-IFG (s) | AGGGGCGACAACAACGTGCCTAGGATCTTCGG CGGCCAGGAATGCAAG (SEQ ID NO: 21) |
| GDX-IFG (a) | CTTGCATTCCTGGCCGCCGAAGATCCTAGGCA CGTTGTTGTCGCCCCT (SEQ ID NO: 22) |
| GDX-IFR (s) | AGGGGCGACAACAACGTGCCTAGGATCTTCAG GGGCCAGGAATGCAAG (SEQ ID NO: 23) |
| GDX-IFR (a) | CTTGCATTCCTGGCCCCTGAAGATCCTAGGCA CGTTGTTGTCGCCCCT (SEQ ID NO: 24) |
| GDX-SFR (s) | AGGGGCGACAACAACGTGCCTAGGAGCTTCAG GGGCCAGGAATGCAAG (SEQ ID NO: 25) |
| GDX-SFR (a) | CTTGCATTCCTGGCCCCTGAAGCTCCTAGGCA CGTTGTTGTCGCCCCT (SEQ ID NO: 26) |
| GDX-SVG (s) | CAACGTGCCTAGGAGCGTGGGCGGCCAGG (SEQ ID NO: 27) |
| GDX-SVG (a) | CCTGGCCGCCCACGCTCCTAGGCACGTTG (SEQ ID NO: 28) |
| GDX-AVG (s) | CCTGAGAGGGGCGACAACAACGTGCCTAGGGC CGTGGGCGGCCAGGAATGCAAGG (SEQ ID NO: 29) |
| GDX-AVG (a) | CCTTGCATTCCTGGCCGCCCACGGCCCTAGGC ACGTTGTTGTCGCCCCTCTCAGG (SEQ ID NO: 30) |

The mutagenesis is carried out by PCR in a volume of 50 μl containing 50 ng (0.2 n) of pNUT-GDX as matrix, 125 ng (70 nM) of each primer (sense and antisense, see Table 4), an equimolar mixture (0.5 mM) of each dNTP, and 2.5 units of Pfu polymerase in the buffer recommended by the manufacturer, using a DNA thermal cycler 480 (PERKIN ELMER). The PCR comprises an initial step of denaturation at 95° C. for 5 minutes, followed by 16 identical cycles which are each made up of 45 seconds of denaturation at 95° C., 60 seconds of hybridization at 55° C., and 26 minutes of elongation at 68° C. At the end of these 16 cycles, the vector having served as matrix is degraded at 37° C. for 60 minutes with 10 units of DpnI.

DH5α bacteria made competent by washing at 4° C. in 100 mM $CaCl_2$ are transformed with 5 to 10 μl of the PCR product digested with DpnI; the colonies which have incorporated a viable plasmid are selected, and the orientation and sequence of the insert are verified.

EXAMPLE 2

Production of the Factor X Derivatives in Eukaryotic Cells

Transfection of BHK-21 Cells:

The recombinant proteins were expressed in newborn hamster kidney cells (BHK-21) provided by the European Collection of Cell Cultures (Sofia-antipolis, France).

The BHK-21 cells are cultured in Petri dishes (80 mm diameter) in an incubator at 37° C. under an atmosphere of 5% $CO_2$, in complete DMEM medium (Dulbecco's Modified Eagle Medium): (GIBCO BRL), supplemented with 10% of foetal calf serum (GIBCO BRL), 2 mM of L-glutamine (GIBCO BRL), 100 units/ml of penicillin (GIBCO BRL) and 100 μg/ml of streptomycin (GIBCO BRL). When they reach approximately 80% confluency, the cells are rinsed twice in PBS buffer (phosphate buffered saline, GIBCO BRL) and then incubated at 37° C. for 1 hour in 4 ml of OPTI-MEM (GIBCO BRL).

The transfection is carried out by adding 40 nM of the expression vector for the desired factor X derivative (40 μg in a volume of 220 μl adjusted with distilled water) to 250 μl of a solution at a pH of exactly 7.05, which is made up of 50 mM Hepes, 1.5 mM $Na_2HPO_4$, 280 mM NaCl, 10 mM KCl and 12 mM dextrose. Coprecipitation of the DNA is obtained by adding 31 μl of 2.5 M $CaCl_2$ dropwise and with constant agitation. After incubation for 30 minutes at ambient temperature, the precipitate is added to the medium covering the cells and left to sediment for 3 hours at 37° C. The cells are washed with PBS (in order to remove most of the precipitate), and returned to culture in complete DMEM medium for 24 hours at 37° C.

The cells are detached from the Petri dish with 2 ml of a solution of 54 mM EDTA, pH 8.0, containing 0.5 mg/ml trypsin, are resuspended in the selection medium (complete DMEM containing 50 mg/l of methotrexate (TEVA, Courbevoie, France)), and are re-seeded into two new Petri dishes. The culture medium is renewed every two days for 2 to three weeks, until colonies are obtained. These colonies are isolated and transferred into the wells (2 cm²) of a 24-well culture plate, where they are multiplied until confluency in the selection medium.

Identification of the Clones Producing a Factor X Derivative:

Detection of the clones stably expressing a factor X derivative is carried out by immunoblotting.

An aliquot (30 μl) of BHK-21 cell culture supernatant, which has remained in contact with the transfected cells for at least 48 hours, is added to 10 µl of 100 mM Tris-HCl, pH 6.8, containing 40% (v/v) of glycerol, 8% (w/v) of SDS, 0.04% (w/v) of bromophenol blue and 20% (v/v) of β-mercaptoethanol. The proteins in the sample are denatured at 95° C. for 5 minutes and are separated on a 12% polyacrylamide gel (crosslinking 29/1) in 25 mM Tris buffer, pH 7.5, containing 0.1 M glycine and 0.1% (w/v) SDS.

The electrophoresis is followed by transfer onto nitrocellulose membrane (TRANS-BLOT, BIO-RAD, Ivry sur Seine, France) in 25 mM Tris-HCl buffer, 0.1 M glycine, pH 7.5, containing 20% methanol. The membrane is saturated by incubation for 1 hour at ambient temperature in a solution of 5% (w/v) skimmed milk in 50 mM Tris buffer, pH 7.5, containing 150 mM of NaCl, 0.1% of Tween 20 (TTBS), and then washed 3 times for 10 minutes in the same buffer. The membrane is then incubated for 1 to 12 hours in the presence of 50 ng/ml of the monoclonal antibody 9E10 in TTBS. After three washes (as previously), the membrane is incubated for one hour at ambient temperature in the presence of an alkaline phosphatase-labelled anti-mouse IgG goat polyclonal antibody (BIO-RAD) diluted to 1/3000 in TTBS. The presence of recombinant protein is revealed by incubation of the membrane in the presence of a chromogenic substrate (mixture in equal amounts of 5-bromo-4-chloro-3-indolyl phosphate, p-toluidine salt (BCIPT) and nitrotetrazolium chloride (NTC), diluted in 0.1 M Tris buffer, pH 9.5, containing 0.5 M of $MgCl_2$).

Cell Culture and Production:

The clones expressing the desired factor X derivative most strongly are amplified, and conserved by freezing in liquid nitrogen (approximately $10^6$ cells in 1 ml of foetal calf serum to which 10% (v/v) DMSO has been added).

Production of the factor X derivatives is carried out in selection medium containing 50 µM of zinc (for induction of the metallothionein promoter) and, for the clones expressing the FX-recombinant derivative possessing a Gla domain, 5 mg/ml of vitamin $K_1$ (ROCHE, Neuilly sur Seine, France) to allow the post-translational γ-carboxylation. The cells are multiplied by successive passages in 150 cm² flasks which are used to inoculate 850 cm² bottles. The culture supernatants are harvested every 2 to 6 days (depending on the cell density), clarified by centrifugation for 10 minutes at 5000 g, and conserved at −20° C. after addition of 5 mM EDTA and 10 mM of benzamidine.

EXAMPLE 3

Purification of the Factor X Derivatives

The purification of the derivatives was carried out in two or three steps, depending on the derivative concerned.

The first step is common to all the purifications: it involves an adsorption onto anion exchange resin in order to concentrate the proteins contained in the culture supernatant.

The culture supernatants are diluted to ⅓ in 50 mM Tris, pH 7.5, containing 10 mM of benzamidine and 5 mM of EDTA. Typically, two litres of supernatant are diluted in four litres of buffer, 4.5 grams of QAE SEPHADEX A50 (AMERSHAM PHARMACIA BIOTECH) are added, and the mixture is stirred slowly for 30 minutes at ambient temperature (using a rotary blade stirrer). The SEPHADEX beads are allowed to sediment for one hour and the supernatant is discarded.

The loaded resin is transferred into a column, and the adsorbed proteins are eluted with 50 mM Tris buffer, pH 7.5, containing 0.5 M NaCl.

The second step is an affinity chromatography which makes it possible to separate the factor X derivative from the other proteins contained in the QAE-SEPHADEX eluate.

The FX-recombinant derivative is purified by affinity chromatography on an AFFI-PREP HZ gel (BIO-RAD) grafted with 3 mg of the monoclonal antibody 9E10 per ml of gel. After loading of the column with the QAE-SEPHADEX eluate and washing in 50 mM Tris buffer, pH 7.5, containing 0.5 M of NaCl, the FX-recombinant derivative is eluted in 0.1 M glycine-HCl buffer, pH 2.7. The pH of the eluate is adjusted to 7.5 by adding 30 µl/ml of 2 M Tris, and the column is re-equilibrated in the washing buffer.

The affinity column grafted with the antibody 9E10 has the drawback of having a low capacity and of requiring elution in denaturing medium. A third purification step, by high-resolution anion exchange chromatography, is necessary in this case in order to remove the denaturing agent and concentrate the derivative eluted from the column.

Several eluates from the affinity column, totaling 2 to 10 mg of FX-recombinant derivative, are pooled, diluted to ¼ in 50 mM Tris buffer, pH 7.5, containing 5 mM EDTA, and loaded onto a Q-SEPHAROSE FAST FLOW column (0.8×10 cm) (AMERSHAM PHARMACIA BIOTECH). After washing in dilution buffer, the column is eluted in 50 mM Tris buffer, pH 7.5, containing 0.5 M NaCl.

Factor X derivatives lacking Gla domain, which carry at their N-terminal end the epitope recognized by the antibody HPC-4, were purified on an affinity column grafted with this antibody. Since the antibody HPC-4 is calcium dependent, the column can be eluted by washing in the presence of a calcium chelator, which does not denature the protein. The factor X derivative thus purified can be used directly.

In this case, the QAE-SEPHADEX eluate is recalcified beforehand at 5 mM by adding $CaCl_2$. The column is washed in 50 mM Tris buffer, pH 7.5, containing 0.5 M of NaCl and 1 mM $CaCl_2$, and the factor X derivative is eluted in 50 mM Tris buffer, pH 7.5, containing 100 mM NaCl and 5 mM EDTA.

In total, a minimum of 10 mg of each of the factor X derivatives was prepared.

Whatever the protocol used, the purity of the preparation is controlled, after denaturation and reduction of a sample, by polyacrylamide gel electrophoresis (12%, crosslinking 29/1) and staining with Coomassie blue.

All the preparations obtained appear to be pure on an SDS-polyacrylamide gel, but two forms are systematically present: a major double-chain form (80 to 90%) with apparent molecular masses compatible with those expected for the heavy and light chains (50 and 23 kDa for the FX-recombinant; 50 and 18 kDa for the derivatives lacking Gla domain); a minor single-chain form (10 to 20% depending on the preparations), with a molecular mass of 66 kDa for the FX-recombinant and 60 kDa for the derivatives lacking Gla domain).

The percentage of single-chain form appears to depend rather on the pool of supernatants from which the preparation is derived than on the mutation introduced: for a given mutation, the percentage of single-chain form varies from one purification to another.

The purified derivatives are aliquoted, and stored at −80° C. until use. The concentration of the aliquot is estimated by its absorbance at 280 nm, taking $1.25 \text{ g}^{-1} \text{ l cm}^{-1}$ to be the molar absorption coefficient ($\epsilon\%_{280}$).

EXAMPLE 4

Thrombin Activation of the Factor X Derivatives

Native factor X can be activated only by its physiological activators (tenase or tissue factor complexes) and by certain snake venoms, the most commonly used of which is Russell's viper venom extract (RVV-X). The Gla domain of factor X plays a very important role in this activation: the rate of activation of normal factor X lacking Gla domain is on average about a hundred times slower than that of complete factor X.

The FX-recombinant behaves essentially like plasma factor X, except that a portion (which is incorrectly γ-carboxylated by the BHK-21 cells) is difficult to activate and is only slightly active within the prothrombinase complex. The factor X derivatives lacking Gla domain remain cleavable (slowly) by the isolated snake venom activator and (to a certain extent) by the physiological complexes.

The ability of the derivatives lacking Gla domain to be cleaved by thrombin was tested.

Two methods were used to evaluate the rate of cleavage of the factor X derivatives by thrombin, depending on whether or not this cleavage generates a detectable amidolytic activity. In the first case, the amidolytic activity generated by the activated factor is measured, and in the second case, the cleaved form is quantified by electrophoresis.

Measuring the Amidolytic Activity:

The rate constants for activation of the factor X derivatives by thrombin are determined under pseudo-first order conditions, i.e. the concentration of the zymogen is at most equal to 0.1 times the concentration for half saturation of the activator (its $K_m$). Under these conditions, the rate constant measured is directly proportional to the specificity constant ($k_{cat}/K_m$) of the activator (thrombin) for its substrate (the zymogen derived from factor X). Without knowing the value of the $K_m$, it is possible to verify that the pseudo-first order condition is respected by measuring the rate of activation at two substrate concentrations: the rate constant measured should be the same (allowing for experimental error) for the two concentrations of zymogen.

Each factor X derivative (between 1 and 10 μm) is incubated in the presence of thrombin (100 nM) in kinetics buffer (50 mM Tris, pH 7.8, containing 150 mM NaCl, 0.2% PEG 8000 (w/v) and 5 mM $CaCl_2$), at 37° C. After varying incubation times, a 10 μl aliquot is sampled, to which 1 μM (100 units per ml) of hirudin (REFLUDAN, HOECHST, Frankfurt, Germany) are added (in order to stop the reaction by neutralizing the thrombin). The amount of active form generated is estimated by the amidolytic activity of the activated derivative. After having added 100 μM of N-α-Z-Arg-Gly-Arg-pNA (S2765, BIOGENIC, Maurin, France), the amidolytic activity is measured by recording the variation in absorbance at 405 nm as a function of time (the initial rate of hydrolysis of the S2765) using an MR5000 microplate reader (DYNEX, Guyancourt, France). Before the addition of thrombin, the rate of hydrolysis of the S2765 is zero since the factor X derivative is entirely in the zymogen form. By plotting the initial rate of hydrolysis of the S2765 as a function of time of incubation of the zymogen with thrombin, a curve is obtained which makes it possible, by non-linear regression, to estimate the rate constant for activation of the zymogen (k), using equation 1 representing a first-order exponential increase:

$$V_t = V_0 + V_{max}(1 - \exp^{(-kt)}) \quad \text{(equation 1)}$$

in which $V_t$ represents the rate of hydrolysis of the chromogenic substrate at time t, $V_0$ the rate of hydrolysis of the chromogenic substrate at time zero (normally zero), and $V_{max}$ the rate of hydrolysis of the chromogenic substrate at infinite time (when all the zymogen is activated). If the pseudo-first order condition is respected, the value of k is equal to the concentration of the activator (thrombin) multiplied by the $k_{cat}/K_m$ for the zymogen activation reaction. This method therefore makes it possible to compare the ability of thrombin to activate the factor X derivatives which generate amidolytic activity after activation. This method is applicable whatever the amidolytic activity generated, with the only condition being that a catalytic activity can be measured: it is in fact the same thing as measuring the percentage activation as a function of time.

Quantification by Electrophoresis

Alternatively, if no catalytic activity is detectable, the ability of thrombin to cleave the factor X derivative is detected on SDS polyacrylamide gel. Incubation of the substrate zymogen with its activator is carried out under the same pseudo-first order conditions as above. After varying incubation times, a 20 μl aliquot is taken, and analysed by polyacrylamide gel electrophoresis (12%, crosslinking 29/1) after denaturation and reduction of the sample.

After staining with Coomassie blue, the gel is scanned and the intensity of each migration band is estimated with imaging software (SCION-IMAGE).

This method makes it possible to evaluate, for each sample, the percentage of each form of the factor X derivative (inactive single-chain, inactive double-chain, activated in α-form, activated in β-form). By plotting the intensity of the bands corresponding to the activated forms as a function of the time of incubation of the zymogen with thrombin, a curve is obtained which makes it possible, by non-linear regression, to estimate the rate constant for activation of the zymogen (k), using equation 1 in which $V_t$, $V_0$ and $V_{max}$ are, respectively, replaced with: the intensity of the band at time t, at time zero (normally zero) and at infinite time (when 100% of the zymogen is activated). If the pseudo-first order condition is respected, the value of k is equal to the concentration of the activator (thrombin) multiplied by the $k_{cat}/K_m$ for the zymogen activation reaction. In practice, it is more reliable to evaluate the disappearance of the zymogen over time. By plotting the intensity of the bands corresponding to the zymogen forms as a function of the time of incubation with thrombin, a curve is obtained which makes it possible, by non-linear regression, using equation 2 below (representing a first-order exponential decrease), to estimate the rate constant for activation of the zymogen:

$$d_t = d_0 + d_{min} \exp^{(-kt)} \quad \text{(equation 2)}$$

In this equation, $d_t$ represents the density at time t, $d_0$ the density at time zero (which is at a maximum), and $d_{min}$ the density at infinite time (which is zero when all the zymogen is activated). If the pseudo-first order condition is respected, the value of k is equal to the concentration of the activator (thrombin) multiplied by the $k_{cat}/K_m$ for the zymogen activation reaction. This method is applicable whatever the factor X derivative considered, but it is less accurate than the chromogenic method.

The results are given in Table V.

The value of the $k_{cat}/K_m$ for the activation of each factor X derivative by thrombin is given, as is the standard error (expressed as percentage of the value obtained).

TABLE V

| Derivative | $k_{cat}/K_m$ ($M^{-1} s^{-1}$) |
|---|---|
| GD-FX | ND |
| GDX-IVG | <1 |
| GDX-IFG | <1 |
| GDX-AVG | $1\ 10^2$ (±9%) |
| GDX-IFR | ND |
| GDX-SVG | <1 |
| GDX-SFR | $4\ 10^3$ (±27%) |

Like its normal plasma homologue, the FX-recombinant is not detectably cleavable by thrombin (ND), as with the GD-FX derivative. On the other hand, the GDX-SFR derivative is cleaved very rapidly by thrombin: the value of the $k_{cat}/K_m$ is $4 \times 10^3$ M$^{-1}$ s$^{-1}$; however, the cleaved derivative lacks amidolytic activity. The GDX-SVG derivative is also cleaved by thrombin, but does not generate detectable amidolytic activity either. The value of the $k_{cat}/K_m$ for the cleavage of the GDX-AVG derivative, by thrombin, is $10^2$ M$^{-1}$ s$^{-1}$, and the activated derivative has readily detectable amidolytic activity. The other factor X derivatives (GDX-IVG, GDX-IFG and GDX-IFR) appear to be thrombin-cleavable, but the reaction is too slow for it to be possible to reliably estimate the value of the $k_{cat}/K_m$.

EXAMPLE 5

Preparation and Characterization of the Activated form of the Factor X Derivatives In order to more thoroughly characterize the catalytic activity (after cleavage) of each of the factor X derivatives, several milligrams of each derivative were activated and purified.

The factor X derivatives carrying at position $P_3$, $P_2$ and $P_1$ of their activation site the sequence LTR (FX-recombinant and GD-FX derivative) are not thrombin-cleavable. They were activated by passing them over a HITRAP NHS-activated column (5 ml) (AMERSHAM PHARMACIA BIOTECH) grafted, at 5 mg/ml of gel, with isolated Russell's viper venom (RVV-X) activator (KORDIA, Leiden, The Netherlands). Four milligrams of factor X derivative in 50 mM Tris buffer, pH 7.5, containing 150 mM NaCl, 5 mM CaCl$_2$ and 0.2% (w/v) PEG 8000, are introduced into the column grafted with RVV-X. The column is closed at both ends and the incubation is sustained for 16 hours at ambient temperature. The activated derivative is eluted with 50 mM Tris, pH 7.5, containing 0.5 M NaCl and 5 mM CaCl$_2$. The eluate contains mainly the activated form but the activation is not always complete. To enrich the eluate in activated form, it is diluted to ⅓ in 50 mM Tris, pH 7.5, containing 5 mM of CaCl$_2$ (to reduce the ionic strength), loaded onto a 1 ml HITRAP heparin-SEPHAROSE column (AMERSHAM PHARMACIA BIOTECH), and eluted with 50 mM Tris buffer, pH 7.5, containing 0.5 M NaCl and 5 mM of CaCl$_2$.

The other factor X derivatives, which can be activated (even slowly) by thrombin, were all activated by passing them over a HITRAP NHS-activated column (1 ml) (AMERSHAM PHARMACIA BIOTECH) grafted, at 1 mg/ml of gel, with thrombin. The incubation conditions (concentration, buffer, temperature and duration) are the same as for the activation by passage through the column grafted with RVV-X, as are the elution from the column and the purification of the activated form of the derivative on heparin-SEPHAROSE.

The N-terminal sequence of the heavy chain produced by activation of the various factor X derivatives was determined by microsequencing. Each sequence obtained corresponds unambiguously to the N-terminal end expected for the heavy chain of the activated form of the derivative considered (IVG, IFG, IFR, AVG, SVG or SFR) after cleavage between the residues $P_1$ and $P_1'$ of the activation site.

Interaction with Chloromethyl Ketone Peptides:

Chloromethyl ketone peptides are irreversible serine protease inhibitors which form an equimolecular and covalent complex with their target. The rate of interaction of a chloromethyl ketone peptide with a protease depends on the sequence which precedes the chloromethyl ketone group. These inhibitors in fact make it possible to evaluate the integrity of the active site of the target: the rate constant for the reaction (the $k_{on}$) is in fact a signature which is specific to each inhibitor/protease pair. One of the chloromethyl ketone peptides most reactive with the activated form of factor X is D-Phe-Phe-Arg-CH$_3$Cl (D-FFR-CK, marketed by CALBIOCHEM, Meudon, France). When the reaction is carried out under pseudo-first order conditions, the $k_{on}$ can be estimated even if the precise concentration of the target is not known. Once the $k_{on}$ is known, it is possible to predict the experimental conditions which will make it possible to accurately titrate the active site concentration for the protease (see below). This titration is a prerequisite for a true functional characterization.

An amount of the activated form of the factor X derivative sufficient to obtain a readily detectable amidolytic activity is incubated, in a reaction volume of 10 µl, for a given period of time in the presence of a fixed concentration of D-FFR-CK in kinetic buffer at 25° C. The concentration of the reagents is in fact very variable: 30 nM to 1.8 µM of activated form (according to the absorbance at 280 nm) depending on the factor X derivative, to have a readily detectable amidolytic activity (10% hydrolysis of the chromogenic substrate in 30 minutes). The concentration of D-FFR-CK added should be much greater than that of its target, such that the reaction occurs under pseudo-first order conditions. The concentration of D-FFR-CK should not, however, be too high, otherwise the reaction is too rapid. Typically, three concentrations of D-FFR-CK are used, which correspond to 10, 20 and 40 times that of the target (estimated by its absorbance at 280 nm). The same experiment is repeated twelve times, varying the incubation time from one experiment to another (from 10 seconds for the first to 5 hours for the last, such that the incubation time for a given experiment is equal to double that of the preceding one). At the end of each incubation, 190 µl of 100 µM S2765 in kinetics buffer are added, and the residual amidolytic activity is measured by recording the variation in absorbance at 405 nm as a function of time (i.e. the initial rate of hydrolysis of the S2765) using an MR5000 microplate reader. By plotting the rate of hydrolysis of the S2765 as a function of time of incubation of the inhibitor with its target, a curve is obtained which makes it possible, by non-linear regression, using equation 2, to estimate the rate constant for inactivation of the activated form of the factor X derivative. The parameters $d_t$, $d_0$ and $d_{min}$ of equation 2 represent, in this case, the residual activity at time t, the initial activity (which is at a maximum) and the activity at infinite time (which is normally zero). If the pseudo-first order condition is respected, the value obtained for k is equal to the concentration of inhibitor multiplied by its $k_{on}$ for the enzyme.

The values of the $k_{on}$ of D-FFR-CK for the activated forms of the factor X derivatives obtained are summarized in Table VI, as is the standard error (expressed as a percentage of the value obtained). The $k_{on}$ for the derivatives lacking catalytic activity cannot be determined by the method used (ND).

TABLE VI

| Derivative | $k_{on}$ (M$^{-1}$ s$^{-1}$) |
|---|---|
| FX-plasma | 2304 (±1%) |
| GD-FX | 2233 (±3%) |
| GDX-IVG | 2250 (±4%) |
| GDX-IFG | 104 (±4%) |
| GDX-AVG | 2 (±10%) |
| GDX-IFR | ND |
| GDX-SVG | ND |
| GDX-SFR | ND |

The value of the $k_{on}$ of the activated form of the FX-recombinant derivative, of the activated form of the GD-FX derivative, and of the activated form of the GDX-IVG derivative are all similar to that obtained with the activated form of the factor X from plasma. This result was expected: the zymogens of these factor X derivatives differ by the presence or absence of a Gla domain and also by the residues $P_3$ and $P_2$ upstream of the activation site, but the catalytic domain of the product of their activation is identical.

The value of the $k_{on}$ for the activated form of the GDX-IFG derivative is 20 times lower; this suggests that the catalytic groove of this factor X derivative is not strictly conserved by the mutation. The value of the $k_{on}$ for the activated form of the GDX-AVG derivative is 1000 times less. The factor X derivatives which, after cleavage, lack detectable amidolytic activity (GDX-IFR, GDX-SVG and GDX-SFR) cannot be analysed by this method.

Titration of the Activated Form of Factor X Derivatives:

The active site concentration for the activated form of the factor X derivatives is a value that is essential to determine in order to be able to evaluate the effective catalytic activity of each mutant. The absorbance at 280 nm indeed makes it possible to calculate the concentration of the purified protease, but it does not provide the proportion of the sample which is in active form. On the other hand, titration makes it possible to estimate the concentration of active form, whatever the percentage of residual zymogen form or the intrinsic activity of the mutant compared to the normal protease.

A very accurate method for titrating serine proteases is based on the use of a chloromethyl ketone peptide, on condition that the enzyme has a measurable catalytic activity and that the half-life of the reaction of the titrating substance with its target can be predicted. Three of the activated forms of factor X derivatives satisfy these criteria, and were titrated by this method: by measuring the residual amidolytic activity after incubation with increasing concentrations of inhibitor. The chloromethyl ketone peptide used is D-FFR-CK, the $k_{on}$ value of which for each target was determined above.

Increasing concentrations of D-FFR-CK, of between 20 nM and 12 µM, are incubated with a fixed amount (0.5 to 1 µM) of the active form of the factor X derivative to be titrated, in kinetics buffer at 25° C. The incubation is sustained until the reaction is complete: i.e. a minimum of 10 half-lives are covered (the half-life of the reaction is equal to the natural logarithm of 2 divided by the product of the $k_{on}$ and the concentration of the inhibitor). At the end of this incubation, 190 µl of 100 µM S2765 in kinetics buffer are added and the residual amidolytic activity is measured by recording the variation in absorbance at 405 nm as a function of time (i.e. the initial rate of hydrolysis of the S2765) using an MR5000 microplate reader. By plotting the rate of hydrolysis of the S2765 as a function of the concentration of D-FFR-CK, a straight line is obtained for which the abscissa at the origin corresponds to the initial concentration of active enzyme (LE BONNIEC et al., Biochemistry, 33, 3959-3966, 1994).

The activated form of the GDX-AVG derivative could not be titrated by this method because the value of the $k_{on}$ of D-FFR-CK ($2 \, M^{-1} \, s^{-1}$) is too low to be able to finish the reaction in a reasonable amount of time: in the presence of one µM of D-FFR-CK, it would be necessary to sustain the reaction for 15 days in order to cover about ten half-lives, whereas the stability of D-FFR-CK does not exceed 48 hours at pH 7.5. The "activated" forms of the factor X derivatives which lack detectable amidolytic activity (GDX-IFR, GDX-SVG and GDX-SFR) could not be titrated either using D-FFR-CK. For these derivatives, the percentage of active form was simply estimated by densitometry after polyacrylamide gel electrophoresis (12%, crosslinking 29/1), after denaturation and reduction of the sample (as described above for identifying the BHK-21 clones producing a factor X derivative). After staining with Coomassie blue, the gel is scanned and the intensity of the bands corresponding to the activated α and β heavy chains is compared to those of the residual uncleaved forms using the analysis software SCION-IMAGE. This method makes it possible to evaluate the percentage of activated form of each aliquot of factor X derivative. By comparing this percentage of activated forms with the total concentration estimated via the absorbance at 280 nm, the effective concentration of activated α and β forms is deduced therefrom.

This method is more laborious than the preceding one, but sufficiently reliable to be able to perform a functional characterization of the mutants concerned.

Amidolytic Activity:

The amidolytic activity of serine proteases involves only their catalytic groove and their charge relay system. It is measured using synthetic substrates made up of a small peptide carrying, at the C-terminal, a para-nitroanilide group; during the hydrolysis of these substrates, para-nitroaniline (pNA), which is readily detectable at 405 nm, is released. These peptides enable a very fine characterization of the catalytic machinery of a protease: the $k_{cat}$ and $K_m$ for the hydrolysis for one of these substrates constitute here again a signature which is unique for each enzyme/substrate pair. Measuring the amidolytic activity of the activated forms of the factor X derivatives therefore made it possible to detect whether or not their catalytic machinery was altered. Two chromogenic substrates were used for this analysis: S2765, and benzyl-CO-Ile-Glu-(γ-OR)-Gly-Arg-pNA (S2222) marketed by BIOGENIC.

The values of the $k_{cat}$ and of the $K_m$ of the activated forms of the factor X derivatives are determined in kinetics buffer, at 25° C. Varying concentrations of substrate (of between 6 and 800 µM) are incubated with a fixed amount of the activated form of the factor Xa derivative (10 nM to 0.5 µM depending on the activated form of the factor X derivative, such that at least 10% of the chromogenic substrate is hydrolysed in 30 minutes). The variation in absorbance at 405 nm as a function of time is recorded using an MR5000 microplate reader, and the initial rate of hydrolysis is estimated by linear regression (only the absorbances corresponding at most to 15% hydrolysis of the substrate are taken into account for the analysis). The value of $k_{cat}$ and of the $K_m$ are estimated by non-linear regression of the variation in initial rate of hydrolysis as a function of the initial concentration of substrate, using the Michaelis-Menten equation.

The values of the $k_{cat}$ and of the $K_m$ and of the $k_{cat}/K_m$ ratio of the S2222 and of the S2765, and also the standard error (expressed as a percentage of the value obtained), for the activated forms of the factor X derivatives are given in Table VII.

These constants cannot be estimated for the derivatives lacking detectable amidolytic activity (ND).

TABLE VII

| Derivative | $K_m$ (µM) | $k_{cat}$ ($s^{-1}$) | $k_{cat}/K_m$ ($M^{-1} s^{-1}$) |
|---|---|---|---|
| Benzyl-CO-Ile-Glu-(γ-OR)-Gly-Arg-pNA (S2222) | | | |
| FX-plasma | 260 (±15%) | 79 (±6%) | $3 \, 10^5$ |
| FX-recombinant | 210 (±5%) | 59 (±2%) | $3 \, 10^5$ |
| GD-FX | 480 (±5%) | 68 (±2%) | $1 \, 10^5$ |
| GDX-IVG | 410 (±6%) | 107 (±3%) | $3 \, 10^5$ |
| GDX-IFG | 1500 (±8%) | 8 (±5%) | $5 \, 10^3$ |

TABLE VII-continued

| Derivative | $K_m$ (µM) | $k_{cat}$ (s$^{-1}$) | $k_{cat}/K_m$ (M$^{-1}$ s$^{-1}$) |
|---|---|---|---|
| GDX-AVG | 1300 (±28%) | 1 (±17%) | 5 10$^2$ |
| GDX-IFR | ND | ND | ND |
| GDX-SVG | ND | ND | ND |
| GDX-SFR | ND | ND | ND |
| N-α-Z-Arg-Gly-Arg-pNA (S2765) | | | |
| FX-plasma | 90 (±24%) | 182 (±7%) | 2 10$^6$ |
| FX-recombinant | 65 (±6%) | 126 (±2%) | 2 10$^6$ |
| GD-FX | 80 (±14%) | 89 (±4%) | 1 10$^6$ |
| GDX-IVG | 75 (±14%) | 153 (±4%) | 2 10$^6$ |
| GDX-IFG | 820 (±6%) | 61 (±3%) | 7 10$^4$ |
| GDX-AVG | 3750 (±21%) | 19 (±18%) | 5 10$^3$ |
| GDX-IFR | ND | ND | ND |
| GDX-SVG | ND | ND | ND |
| GDX-SFR | ND | ND | ND |

The values of the $k_{cat}$ and of the $K_m$ for the activated form of the FX-recombinant derivative, those of the activated form of the FX-recombinant lacking Gla domain, and those of the GDX-IVG derivative are similar to those obtained for the activated form of the factor X from the plasma (they differ at most by a factor of two). Besides the C-terminal epitope, the catalytic domain which is formed during the activation of these factor X derivatives is identical; thus, as for the $k_{on}$ of D-FFR-CK, it was expected that their amidolytic activities would be at least comparable. It is interesting to note that the absence of the Gla domain has no notable effects on the amidolytic activity of the activated form of the derivative; this suggests that it does not influence the structure of the catalytic groove of the activated form of the factor X. By comparison, the value of the $k_{cat}$ of the activated form of the GDX-IFG derivative is decreased (10-fold for S2222 and 3-fold for S2765); the value of the $K_m$ is similarly increased (5- to 10-fold). Overall, the $k_{cat}/K_m$ for these chromogenic substrates is 30 to 50 times smaller than for the activated form of normal factor X, a decrease which is therefore of the same order of magnitude as that observed for the $k_{on}$ of D-FRR-CK (2-fold). The decrease in the value of the $k_{cat}$ of the activated form of the GDX-AVG derivative is in much greater proportion (about a hundred-fold for S2222, about ten-fold for S2765), as is the increase in the $K_m$ (5 times higher for S2222, 40 times higher for S2765). Overall, the $k_{cat}/K_m$ for these chromogenic substrates is 400 to 600 times smaller than for the activated form of normal factor X; these values are in agreement with the decrease observed for the $k_{on}$ of D-FFR-CK (1000-fold). These results confirm that the mutations carried by the GDX-IFG and GDX-AVG derivatives clearly induce structural modifications in the catalytic groove and/or disturb the activity of the charge relay system.

Activity Within the Prothrombinase Complex:

Native factor Xa is not a very active enzyme compared to trypsin or to thrombin. Physiologically, it is only when the enzyme binds to its cofactor (clotting factor Va), in the presence of phospholipids and calcium, that the prothrombin activation reaction becomes very rapid (the reaction is thousands of times more rapid in the presence of the cofactors than in their absence). The activity within the prothrombinase complex is however greatly dependent on the presence of a Gla domain: without it, the rate is increased at most only 50 times. This difference is, however, largely sufficient to make it possible to detect whether or not the activated form of the factor X derivatives interacts with factor Va, and especially whether or not the cofactor enables it to effectively activate prothrombin. The inventors have therefore compared the rate of activation of prothrombin by each of the activated forms of the factor X derivatives, in the presence, as well as in the absence, of factor Va, of phospholipids and of calcium.

The cofactor effect of factor Va (KORDIA) is studied in a strictly controlled purified system: the prothrombin in particular is immunopurified (LE BONNIEC et al. J. Biol. Chem., 266, 13796-803, 1991; LE BONNIEC et al., 1992, mentioned above), in order to be free of any trace of activated form (factor X or of thrombin). The activation of this prothrombin is detected by the formation of thrombin which results therefrom. The reaction is continuously followed by virtue of the presence in the reaction medium of a chromogenic substrate, H-D-Phe-Pip-Arg-pNA (S2238, BIOGENIC), which is much more sensitive to thrombin than the activated form of factor X. At time zero, there is no thrombin and there is only insignificant hydrolysis of the S2238 by the activated form of the factor X derivative. During the reaction, the thrombin concentration increases in a linear fashion over time (when the reaction for activation of prothrombin by the activated form of the factor X derivative is in steady state). The rate of hydrolysis of the S2238 is directly proportional to the thrombin concentration, but this increases over time. The rate of cleavage is not therefore constant; it goes increasingly quickly: the reaction accelerates. It is possible to show (KOSOW, Thromb. Res. Suppl., 4, 219-227, 1974) that the amount of pNA released by the hydrolysed S2238 (therefore the absorbance at 405 nm of the mixture) is proportional to the coefficient of acceleration of the reaction multiplied by the time squared; the coefficient of acceleration itself being directly proportional to the initial rate of thrombin formation. In practice, 195 µl of kinetics buffer containing 100 µM of S2238, 0.5 µM of prothrombin and 35 µM of phospholipid vesicles (mixture of phosphatidylserine and phosphatidylcholine in a proportion of 20%-80% w/w), in the presence or absence of 20 nM of factor Va, are preincubated at 37° C. in a microtitration plate. The reaction is triggered by adding 2.5 nM of the activated form of the factor X derivative (5 µl at 50 nM), and the variation in absorbance at 405 nm as a function of time is recorded using an MR5000 microplate reader. By plotting the absorbance at 405 nm as a function of incubation time, a curve is obtained which makes it possible, by non-linear regression, to estimate c, the coefficient of acceleration of the reaction, using equation 3:

$$A_{405} = A_0 + bt + ct^2 \quad \text{(equation 3)}$$

in which $A_0$ represents the initial absorbance of the mixture at 405 nm (before addition of the enzyme), and b the rate of hydrolysis of the S2238 by the activated form of the factor X derivative (which is negligible in practice). If the reaction for activation of prothrombin by the activated form of the factor X derivative is in steady state, and if the residual concentration of non-hydrolysed S2238 remains very much greater than its $K_m$ for thrombin (3.6 µM), the parameter c is effectively proportional to the initial rate of activation of prothrombin by the activated form of the factor X derivative. In order to satisfy these conditions, only the experimental points corresponding to less than 15% hydrolysis of each substrate (prothrombin and S2238) are taken into account for analysis by non-linear regression. This approach does not make it possible to estimate the catalytic constants for the activation of prothrombin by the activated form of the factor X derivatives; it only makes it possible, when the reaction is carried out under identical conditions, to compare the activity of two enzymes (here the activity of each activated form of factor X derivatives is compared to that of the activated form lacking Gla domain which serves as reference).

The results obtained are summarized in Table VIII.

The coefficients of acceleration of pNA release by the thrombin generated by the prothrombinase complex (+factor Va) or by the activated factor X derivative alone (−factor Va) are indicated, along with the standard error (expressed as a percentage of the value obtained).

TABLE VIII

| Derivative | +factor Va | −factor Va |
|---|---|---|
| GD-FX | $4.2\ 10^{-4}$ (±2%) | $8.8\ 10^{-6}$ (±2%) |
| GDX-IVG | $1.1\ 10^{-4}$ (±1%) | $2.8\ 10^{-5}$ (±2%) |
| GDX-IFG | $4.9\ 10^{-6}$ (±1%) | $1.0\ 10^{-7}$ (±2%) |
| GDX-AVG | $3.1\ 10^{-5}$ (±1%) | $9.6\ 10^{-7}$ (±2%) |
| GDX-IFR | $3.3\ 10^{-6}$ (±1%) | ND |
| GDX-SVG | ND | ND |
| GDX-SFR | ND | ND |

In the presence of phospholipids and calcium (but in the absence of factor Va), the activation of the prothrombin is very slow and difficult to detect, including for the activated form of factor X lacking Gla domain or that of its GDX-IVG derivative; the addition of factor Va increases the rate of activation of the prothrombin 50-fold and 10-fold respectively. In the absence of factor Va, activation of the prothrombin is detectable for none of the other activated forms of factor X derivatives (GDX-AVG, GDX-IFG, GDX-IFR, GDX-SVG and GDX-SFR). The addition of factor Va makes it possible to considerably increase the rate of activation of the prothrombin by the activated form of the GDX-AVG derivative: this is now only 13 times less than that obtained for the activated form of its non-mutated homologue (GDX-IVG). It therefore appears that factor Va in large part restores the catalytic activity of the activated form of the GDX-AVG derivative, since, compared to its non-mutated homologue, the catalytic groove probes (D-FFR-CK, S2765 and S2222) reflect an efficiency of catalysis which is decreased by at least 400-fold. With the other activated forms of factor X derivatives (GDX-IFG, GDX-IFR, GDX-SVG and GDX-SFR), the addition of factor Va is far from having such effect: it still does not make it possible to detect any activation of prothrombin (ND).

Inhibition by Antithrombin:

The most powerful plasma inhibitor of the activated form of factor X is tissue factor pathway inhibitor (TFPI); the value of its $k_{on}$ for the interaction with the activated form of factor X is greater than $10^5\ M^{-1}\ s^{-1}$. However, the plasma concentration of TFPI (2.5 nM) means that this inhibitor plays a relatively minor role in inhibiting the activated form of factor X (its physiological target is rather clotting factor VIIa).

Antithrombin (alone) is a relatively less powerful inhibitor since the value of its $k_{on}$ for the interaction with the activated form of factor X is only of the order of $10^4\ M^{-1}\ s^{-1}$. The plasma concentration of antithrombin (2.3 µM) makes it, however, the main physiological inhibitor of factor Xa: at this concentration, the plasma half-life of the activated form of factor X would be only 30 seconds (we have experimentally measured one minute, see below). In particular, in the presence of heparin, the value of the $k_{on}$ of antithrombin for the interaction with the activated form of factor X exceeds $10^6\ M^{-1}\ s^{-1}$, i.e. for an antithrombin plasma concentration of 2.3 µM, neutralization of the protease occurs in a few seconds (the half-life would now be only 0.3 seconds). It was therefore essential to determine the $k_{on}$ of the interaction of antithrombin with the activated forms of the factor X derivatives, since any increase in the plasma half-life would prolong the procoagulant action of the factor X derivative, and would therefore potentiate its anti-haemophilic effect.

The inventors determined the ability of each activated form of the factor X derivatives to form a stable covalent complex with antithrombin. They also estimated the value of the $k_{on}$ of antithrombin (in the presence and absence of heparin) for the activated forms of factor X derivatives having detectable amidolytic activity (derivative lacking Gla domain, and GDX-IVG, GDX-IFG and GDX-AVG derivatives).

The demonstration of covalent complexes between the activated form of the factor X derivatives (1 µM) and the antithrombin (2 µM; purified from human plasma according to the technique described by MCKAY (Thromb. Res., 21, 375-382, 1981)) is carried out in the presence of 2 units/ml of heparin (KORDIA). The incubation is sustained for one hour at 25° C., and the reaction mixture is analysed by polyacrylamide gel electrophoresis (10%, crosslinking 29/1), after denaturation and reduction of the sample. After staining with Coomassie blue, the presence of covalent complexes between the (inactivated) form of the factor X derivative and the antithrombin results in a decrease in the intensity of the band corresponding to antithrombin (60 kDa), a decrease in the intensity of the band corresponding to the activated form of the factor X derivative (31 kDa), and the appearance of a new band of higher molecular weight (approximately 100 kDa) corresponding to the covalent complex.

Figure 3:
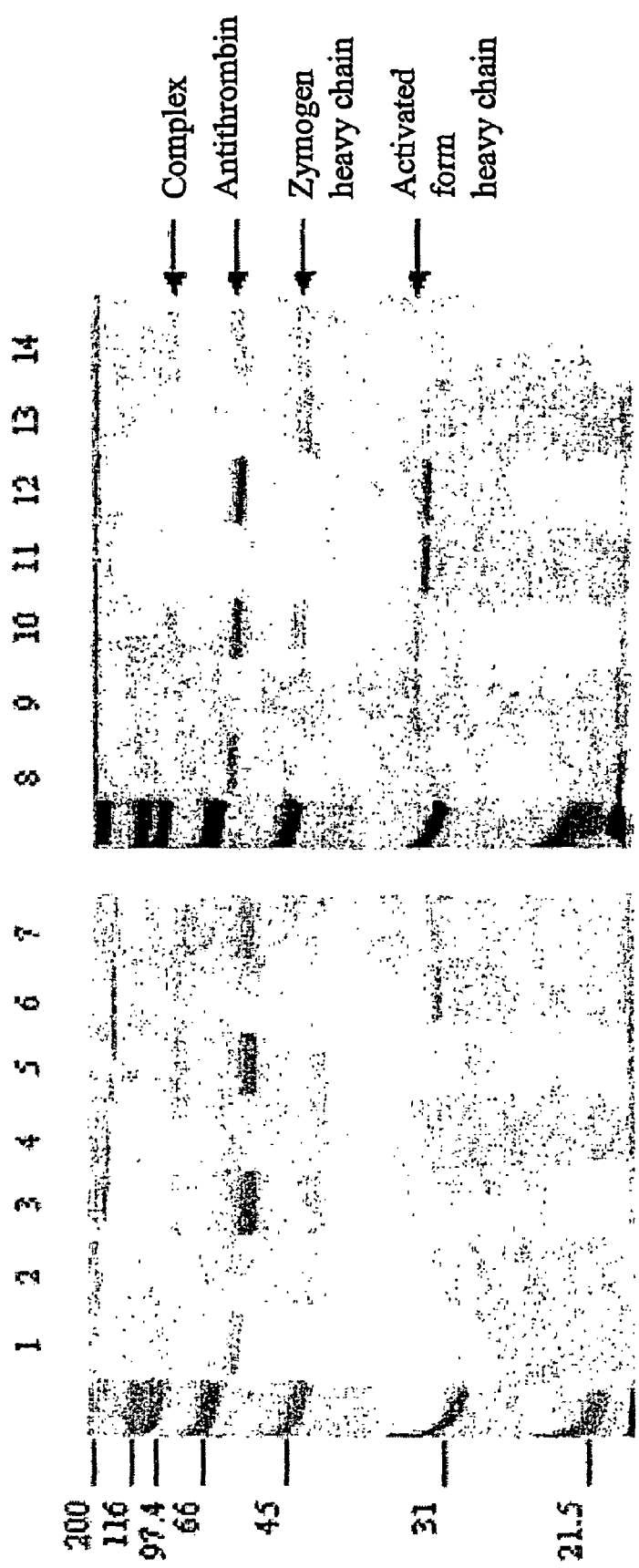
FIG. 3 shows the covalent complexes that form between the activated form of the factor X derivatives and antithrombin. Lanes 1 and 8: antithrombin alone; lanes 2 and 3: GDX-IVG derivative without and with antithrombin; lanes 4 and 5: GDX-IFG derivative without and with antithrombin; lanes 6 and 7: GDX-IFR derivative without and with antithrombin; lanes 9 and 10: GDX-SVG derivative without and with antithrombin; lanes 11 and 12: GDX-SFR derivative without and with antithrombin; lanes 13 and 14: GDX-AVG derivative without and with antithrombin. The formation of a complex results in the appearance of a high molecular weight band (lanes 3, 5, 7, 10 and 14), which is absent when the antithrombin (lanes 1 and 8), or one of the activated forms of the factor X analogues (lanes 2, 4, 6, 9, 11, 13) are used alone. A single factor X analogue (GDX-SFR, lane 12) does not allow formation of a detectable covalent complex.

The results are given in FIG. 3.

Lanes 1 and 8: antithrombin alone; lanes 2 and 3: GDX-IVG derivative without and with antithrombin; lanes 4 and 5: GDX-IFG derivative without and with antithrombin; lanes 6 and 7: GDX-IFR derivative without and with antithrombin; lanes 9 and 10: GDX-SVG derivative without and with antithrombin; lanes 11 and 12: GDX-SFR derivative without and with antithrombin; lanes 13 and 14: GDX-AVG derivative without and with antithrombin.

The formation of a complex results in the appearance of a high molecular weight band (lanes 3, 5, 7, 10 and 14), which is absent when the antithrombin (lanes 1 and 8), or one of the activated forms of the factor X analogues (lanes 2, 4, 6, 9, 11, 13) are used alone. A single factor X analogue (GDX-SFR, lane 12) does not allow formation of a detectable covalent complex.

All the activated forms of the factor X derivatives (except the GDX-SFR derivative) are therefore capable, in the presence of heparin, of forming a stable covalent complex with antithrombin, including the GDX-SVG derivative, which is nevertheless devoid of any detectable catalytic activity.

The method selected for estimating the $k_{on}$ of antithrombin for the activated form of the factor X derivative depends on the half-life of the reagents. The method is not the same depending on whether the half-life is greater than three minutes, between 15 seconds and three minutes, or less than 15 seconds. The reaction must be carried out (unless this is impossible, see below) under pseudo-first order conditions: i.e. the concentration of the inhibitor (antithrombin) must be a minimum of 10 times that of its target (the activated form of the factor X derivative). Moreover, the concentration of the target should be sufficient to be able to readily detect its residual amidolytic activity (10 nM to 1 µM depending on the activated form of the factor X derivative, such that, ideally, 10% of the chromogenic substrate is hydrolysed in 30 minutes). These two constraints considerably limit the choice of the concentration of the reagents: the concentration of antithrombin should be at least from 0.1 to 10 µM (depending on the target). The half-life of the target (equal to the natural logarithm of 2 divided by the product of the concentration of the inhibitor and its $k_{on}$ for the target) determines the method to be used. For half-lives greater than three minutes, the method used is the same as that described for estimating the $k_{on}$ of D-FFR-CK: it consists in determining the residual activity contained in aliquots taken at varied times, so as to cover about ten half-lives. For antithrombin concentrations between 0.1 and 10 μM, this approach makes it possible to estimate only $k_{on}$ values which are at most equal to $2 \cdot 10^4 \, M^{-1} \, s^{-1}$. When the half-life of the reaction is less than three minutes, the batchwise measurement of the residual activity (by sampling aliquots) becomes difficult to put into practice. In this case, still with antithrombin concentrations between 0.1 and 10 μM (therefore $k_{on}$ values greater than $2 \cdot 10^4 \, M^{-1} \, s^{-1}$), the reaction is followed continuously by virtue of the presence in the reaction medium of S2765. The rate of hydrolysis of the S2765 is directly proportional to the residual concentration of the activated form of factor X. At time zero, the amidolytic activity is at a maximum since no inhibition has yet occurred. If the pseudo-first order conditions are respected, the concentration of the activated form of the factor X derivative decreases over time, according to a first-order decreasing exponential. The rate of cleavage is not constant: it slows down until it becomes zero (when all the target has been neutralized). It is possible to show (CHA, Biochem. Pharmacol., 24, 2177-2185, 1975; STONE & HOFSTEENGE, Biochemistry, 25, 4622-4628, 1986) that the amount of pNA released by the hydrolysis of the S2765 (therefore the absorbance at 405 nm of the reaction mixture) increases according to a first-order exponential increase, which can be analysed by non-linear regression using equation 4:

$$A_{405} = A_0 + V_i(1 - \exp^{(-Ikt)})/k \quad \text{(equation 4)}$$

in which $A_0$ represents the initial absorbance at 405 μm, $V_i$ the rate of hydrolysis of the S2765 in the absence of antithrombin, I the concentration of antithrombin, and k the pseudo-first order rate constant for the inhibition reaction. During the reaction, the inhibitor is in competition with the substrate for the interaction with the enzyme; thus, the value of the $k_{on}$ of antithrombin for the activated form of the factor X derivative is related to k by the equation:

$$k_{on} = k(1 + S/K_m) \quad \text{(equation 5)}$$

in which S represents the initial concentration of the chromogenic substrate (S2765) and $K_m$ its Michaelis constant for the activated form of the factor X derivative (determined during the characterization of the amidolytic activity). This method makes it possible to measure half-lives in the order of 15 seconds, i.e. to estimate $k_{on}$ values at most equal to $2 \cdot 10^5 \, M^{-1} \, s^{-1}$ (for antithrombin concentrations between 0.1 and 10 μM). For concentrations of activated forms of the factor X derivatives between 10 nM and 1 μM, when the half-life of the reaction is less than 15 seconds, the amplitude of the signal (the absorbance at 405 nm) is too small to allow reliable continuous measurement of the residual activity (increasing the concentration of the enzyme would require that of the antithrombin to be increased in order to respect the pseudo-first order condition, and therefore the half-life to be further decreased). Thus, when the on is greater than $2 \cdot 10^5 \, M^{-1} \, s^{-1}$, the reaction is no longer carried out under pseudo-first order conditions, but under second-order conditions. The pseudo-first order condition means that the concentration of the antithrombin remains (in appearance) constant throughout the reaction; this is the case when it is in great excess compared to the target. If the concentration of the inhibitor is less than ten times greater than that of its target, the decrease in the concentration of the inhibitor (by formation of a complex with its target) can no longer be ignored. During the reaction, the concentrations of the inhibitor and of its target both vary over time, which greatly complicates the analysis. It remains possible, however, to obtain a sufficient signal amplitude and to follow the kinetics of the inhibition in the presence of a chromogenic substrate under second-order conditions. It is possible to show that, in this case, the absorbance at 405 nm of the reaction mixture increases according to a curve which can be analysed by non-linear regression using equation 6, termed "slow tight-binding inhibition" (CHA, 1975, mentioned above; Biochem. Pharmacol, 25, 2695-2702, 1976; WILLIAMS and MORRISON, Methods Enzymol, 63, 437-467, 1979):

$$P = V_s t + (V_0 - V_s)(1-d)/(dk') \ln\{(1 - d\exp^{(-k't)})/(1-d)\} \quad \text{(equation 6)}$$

in which P represents the concentration of pNA released at time t (directly proportional to the absorbance at 405 nm), $V_0$ the rate of hydrolysis of the S2765 in the absence of the inhibitor, and $V_s$ the final rate of hydrolysis of the S2765 (when the reaction has finished). The parameters d and k' themselves depend on two parameters ($F_1$ and $F_2$) such that:

$$d = (F_1 - F_2)/(F_1 + F_2);$$

$$k' = kF_2;$$

$$F1 = K_I' + I + E;$$

$$F_2(F_1^2 - 4 \, EI)^{1/2}.$$

In these equations, I represents the initial concentration of antithrombin, E that of the target, and $K_I'$ the apparent inhibition constant for the interaction. The $k_{on}$ of the antithrombin for the activated form of the factor X derivative is related to k (which has the same meaning as in equation 4) by the relationship given in equation 5.

The method by batchwise sampling of aliquots is used to estimate the $k_{on}$ of the antithrombin for the activated form of the GDX-AVG derivative (in the presence and the absence of heparin).

The reaction is carried out in kinetics buffer containing 1 mg/ml of protease-free bovine albumin (SIGMA, St Quentin-Fallavier, France) and, when appropriate, 2 units per ml of heparin (KORDIA). In a reaction volume of 10 μl, a sufficient amount of the activated form of the GDX-AVG derivative (0.5 μM in the presence of heparin, 1 μM in its absence) is incubated in the presence of a large excess of antithrombin (5 μM in the presence of heparin, 10 μM in its absence), for a varying amount of time at 25° C. The same experiment is repeated twelve times, varying the incubation time from one experiment to another (from 10 seconds for the first to 5 hours for the last, such that the incubation time for a given experiment is equal to double that of the preceding one). At the end of each incubation, 190 μl of S2765 (200 μM in kinetics buffer) are added, and the residual amidolytic activity is measured by recording the variation in the absorbance at 405 nm as a function of time (i.e. the initial rate of hydrolysis of the S2765) using an MR5000 microplate reader. By plotting the rate of hydrolysis of the S2765 as a function of time of incubation of the inhibitor with its target, a curve is obtained which makes it possible, by non-linear regression using equation 2, to estimate the rate constant for inactivation of the activated form of the factor X derivative. The parameters $d_t$, $d_0$ and $d_{min}$ of equation 2 represent, respectively: the residual activity at time t, the initial activity (which is at a maximum), and the activity at infinite time (which is usually zero). If the pseudo-first order condition is respected, the value obtained for k is equal to the concentration of the inhibitor multiplied by the $k_{on}$ of the reaction for inactivation of the activated form of the factor X derivative.

The method by continuous recording of the absorbance at 405 nm under pseudo-first order conditions is used to estimate (in the absence of heparin) the $k_{on}$ of the antithrombin for the activated form of the factor X derivative lacking Gla domain, and those of the activated forms of the GDX-IVG and GDX-IFG derivatives.

The kinetics are studied at 25° C., in kinetics buffer containing 1 mg/ml of protease-free bovine albumin, and followed continuously by virtue of the presence in the reaction medium of 100 µM of S2765. The reaction is carried out in a microplate, in a volume of 200 µl, if the amplitude of the signal makes it possible to follow the kinetics with a plate reader. If this is not the case, reaction is carried out in a 600 µl microcuvette, and the kinetics followed using a spectrophotometer (LAMBDA 14, PERKIN-ELMER (Courtaboeuf, France)). The reaction is triggered by adding 10 to 25 nM of the activated form of the factor X derivative (ideally such that, in the absence of inhibitor, 10% of the chromogenic substrate is hydrolysed in 60 minutes). For each activated form of factor X derivative, the reaction is carried out in the presence of three concentrations of antithrombin, equal to 10, 20 and 40 times the concentration of the target. By plotting the absorbance at 405 nm as a function of time, a curve is obtained which makes it possible, by non-linear regression using equation 4 (representing a first-order exponential growth), to estimate the rate constant for inactivation of the activated form of the factor X derivative. If the pseudo-first order condition is respected, the $k_{on}$ of the antithrombin for the activated form of the factor X derivative is given by equation 5 which takes into consideration the competition introduced by the substrate during the kinetics.

In the presence of heparin, if the pseudo-first order conditions are respected, the half-life of the activated form of the factor X derivative lacking Gla domain, and also that of the activated forms of the GDX-IVG and GDX-IFG derivatives, are less than 15 seconds. Decreasing the concentrations of antithrombin and of its target could make it possible to respect the pseudo-first order condition while at the same time increasing the half-life, but would reduce the amplitude of the signal; now, the sensitivity of the spectrophotometer becomes insufficient to follow continuous kinetics when the amplitude is only a few milli-units of absorbance. Consequently, the kinetics of the inhibition by the antithrombin, in the presence of heparin, of the activated form of the factor X derivative lacking Gla domain, and also of the activated forms of the GDX-IVG and GDX-IFG derivatives, are followed under second-order conditions.

The kinetics are studied at 25° C., in kinetics buffer containing 1 mg/ml of protease-free bovine albumin and 2 units per ml of heparin; they are followed continuously by virtue of the presence in the reaction medium of 400 µM S2765. The reaction is carried out in a microcuvette in a volume of 600 µl, following the kinetics using a lambda 14 spectrophotometer. The reaction is triggered by adding the minimum amount of activated form of the factor X derivative which is compatible with a reliable signal (1 to 2.5 nM depending on the derivative, such that, in the absence of inhibitor, approximately 10% of the chromogenic substrate is hydrolysed in 60 minutes). For each activated form of factor X derivative, the reaction is carried out in the presence of two concentrations of antithrombin, equal to 2 and 3 times the concentration of the target. By plotting the absorbance at 405 nm as a function of time, a curve is obtained which makes it possible, by non-linear regression using equation 6, to estimate the second-order rate constant for the reaction. The $k_{on}$ of the antithrombin for the activated form of the factor X derivative is given by equation 5 which takes into consideration the competition introduced by the substrate during the kinetics.

The results obtained are summarized in Table IX. The values of the $k_{on}$ (in $M^{-1} s^{-1}$) of the antithrombin in the presence of heparin (+heparin) or in its absence (−heparin) are indicated, along with the standard error (expressed as a percentage of the value obtained).

TABLE IX

| | $k_{on}$ ($M^{-1} s^{-1}$) | |
| --- | --- | --- |
| Derivative | −heparin | +heparin |
| GD-FX | $1.2\ 10^4$ (±4%) | $1.3\ 10^7$ (±1%) |
| GDX-IVG | $5.8\ 10^3$ (±3%) | $2.0\ 10^7$ (±1%) |
| GDX-IFG | $1.8\ 10^2$ (±2%) | $7.6\ 10^5$ (±1%) |
| GDX-AVG | 10.0 (±17%) | $3.0\ 10^2$ (±6%) |
| GDX-IFR | ND | ND |
| GDX-SVG | ND | ND |
| GDX-SFR | ND | ND |

In the absence of heparin, the values for $k_{on}$ of the antithrombin for the activated form of the factor X derivative lacking Gla domain and the activated form of the GDX-IVG derivative are similar (they differ at most by a factor of two). In comparison, the value for the $k_{on}$ of the antithrombin for the activated form of the GDX-IFG derivative is 66 times smaller. In particular, the value for the $k_{on}$ for the activated form of the GDX-AVG derivative is more than 1000 times less than that of its non-mutated homologue (the inhibition is in fact difficult to detect). In the presence of heparin, the value for the $k_{on}$ of the antithrombin for the activated derivatives of factor X increases 1000- to 4000-fold, while, even in the presence of heparin, the $k_{on}$ of the antithrombin for the activated form of the GDX-AVG derivative does not exceed $3\ 10^2\ M^{-1}\ s^{-1}$. This important observation suggests that, after activation, the GDX-AVG derivative might remain active for much longer than its non-mutated homologue (its plasma half-life might be several hours in the absence of heparin, 17 minutes in its presence).

Plasma Half-Life of the Activated Form of the Factor X Derivatives:

The $k_{on}$ of the antithrombin for the activated form of the factor X derivatives suggests that the plasma half-life of the activated form of the GDX-AVG derivative might be considerably extended, which would reinforce its anti-haemophilic potential. In order to verify this hypothesis, the inventors determined the plasma half-life of the activated form of each of the factor X derivatives.

The plasma half-life of the activated forms of the factor X derivatives is estimated by measuring their residual activity after incubation for a varying amount of time in a pool of normal human plasmas. To prevent the formation of a clot, the pool of plasma is rendered unclottable by adding 0.8 µM of hirudin (80 units per ml) before being recalcified (by adding 8 mM $CaCl_2$). The reaction mixture is made up of 80% (v/v) of plasma and 20% (v/v) of kinetics buffer containing hirudin, calcium and the activated form of one of the factor X derivatives at a concentration sufficient to allow its detection (20 to 300 nM final concentration). After varying incubation times, an aliquot (40 µl) is removed, and the residual amidolytic activity is measured, after having added 160 µl of S2765 (1 mM for the activated form of the GDX-AVG derivative, 100 µM for the other activated forms of factor X derivatives), by recording the variation in the absorbance at 405 nm as a function of time (initial rate of hydrolysis of the S2765) using an MR5000 microplate reader. The rate constant for the decrease in the activity is estimated by non-linear regression of the variation in the residual activity as a function of time using equation 2, in which $d_t$, $d_0$ and $d_{min}$ represent the residual activity at time t, the initial activity (which is at a maximum), and the activity at infinity time (which is at a minimum), respectively. Although the hirudin neutralizes any trace of thrombin, the minimum activity is not zero even if all the activated form of factor X is neutralized: this background noise comes from other proteases contained in the plasma, capable of slowly hydrolysing the S2765. If the pseudo-first order condition is respected, the plasma half-life is equal to the ratio of the natural logarithm of 2 over k (the rate constant for decrease). The plasma half-life observed depends neither on the concentration of the target nor on the amplitude of the amidolytic activity measured, it depends only on the initial concentration of the inhibitor contained in the plasma (and, of course, on its reactivity with respect to the target): if the antithrombin is indeed the main plasma inhibitor involved, the pseudo-first order condition is respected since, during the entire incubation, it remains in large excess (1.8 µM) compared to its target.

The results obtained are summarized in Table X. The values for the half-life (in minutes) of the activated form of the factor X derivatives in the presence of heparin (+heparin) or in its absence (−heparin) are given, as is the standard error (expressed as a percentage of the value obtained). The half-life of the activated forms of derivatives lacking detectable amidolytic activity was not determined (ND).

TABLE X

| Derivative | Half-life (minutes) | |
| --- | --- | --- |
|  | −heparin | +heparin |
| GD-FX | 1.1 (±2%) | <0.5 |
| GDX-IVG | 1.1 (±19%) | <0.5 |
| GDX-IFG | 12.5 (±5%) | <0.5 |
| GDX-AVG | >60 | 5.5 (±19%) |
| GDX-IFR | ND | ND |
| GDX-SVG | ND | ND |
| GDX-SFR | ND | ND |

In the absence of heparin, the plasma half-life of the activated form of factor X lacking Gla domain and of the activated form of the GDX-IVG derivative are comparable (one minute); in the presence of heparin, the plasma half-life of these activated forms is too short to be reliably measured. In the absence of heparin, the half-life of the activated form of the GDX-AVG derivative is notably extended: it is 55 times longer than that of the activated form of factor X lacking Gla domain. The increase in the plasma half-life in the presence of heparin is also notable since it can be easily measured (5 minutes and 30 seconds), unlike that of its non-mutated homologue. The plasma half-life of the activated form of the GDX-IFG derivative is also extended (12-fold compared to that of the activated form of factor X lacking Gla domain). The plasma half-life of the other activated forms of factor X derivatives (lacking amidolytic activity) cannot be estimated by the method used.

EXAMPLE 6

Anti-Haemophilic Activity of the Factor X Derivatives

The procoagulant activity of the activated forms of the factor X derivatives was tested in plasmas simulating severe haemophilia A or B. These plasmas are obtained by depleting a normal plasma of factor VIII or IX, and behave, in vitro, like authentic plasmas from haemophiliacs. The factor X analogues tested (GDX-IVG, GDX-IFG, GDX-AVG, GDX-IFR, GDX-SFR, GDX-SVG) all lack a Gla domain. In normal plasma, the procoagulant action of factor X lacking Gla domain is much less than that of normal factor X, because the Gla domain contributes to the activity of the prothrombinase complex.

The procoagulant activity of these factor X derivatives cannot be comparable to that of normal factor X. In fact, any factor X derivative lacking Gla domain is an inhibitor of the prothrombinase complex; specifically, it competes with the activated form of plasma factor X, which, having its Gla domain, is much more active. In other words, in a normal plasma, the addition of any factor X derivative lacking Gla domain delays the formation of a clot rather than promoting it.

The fact that the procoagulant activity of the derivatives lacking Gla domain is much less than that of normal factor X does not, however, prevent comparisons being made between these derivatives. Specifically, the contribution of the Gla domain in the procoagulant activity is uniform whatever the derivative: it is independent of its catalytic activity. A factor X derivative which, compared to the normal derivative, decreases the "clotting time" (time required for the plasma to lose its fluidity) therefore reflects a better procoagulant activity, an increase in the clotting time indicates, on the other hand, that the derivative is less active than its normal homologue. The procoagulant activity of the factor X derivatives (activated or not) was therefore compared with that of the normal homologue lacking Gla domain (GD-FX).

Procoagulant Effect of the Activated Forms of the Factor X Derivatives:

Addition of the activated form of a factor X derivative to plasma from a haemophiliac does not test the cyclization of the activation of prothrombin: it only reflects the ability of the activated derivative to function under conditions close to those encountered in vivo. In the absence of tissue factor and of factor VIII or IX, no amplification of the clotting cascade takes place, only the activated form of the factor X derivative enables the formation of thrombin and, subsequently, the formation of a clot. The study of the activity within the prothrombinase complex (cf. Example 5) shows that the addition of activated factor V partly restores the catalytic activity of the activated form of the GDX-AVG analogue: it is now only 13 times less than that of its non-mutated homologue (GDX-IVG). This effect is far from being as marked with the other activated forms of factor X analogues (GDX-IFG, GDX-IFR, GDX-SVG and GDX-SFR). The use of factor VIII- or factor IX-depleted plasma makes it possible to study the possible interference with other clotting factors, in particular the effect of the regulatory mechanisms (antithrombin, etc.).

The procoagulant effect of the activated form of the factor X derivatives is detected by the ability to induce the formation of a clot in a factor VIII- or factor IX-depleted plasma (DIAG-NOSTICA STAGO, Asnières, France). By adding tissue factor to one of these plasmas, it is possible to trigger the formation of sufficient thrombin to induce the formation of a clot, but the clotting time is extremely long and cannot be measured with conventional methods. Thus, the reaction is carried out in a microplate, and the clot formation is followed by turbidimetry, recording the optical density at 405 nm as a function of time (whatever the wavelength, the absorbance increases with the turbidimetry). The clot formation, which is relatively abrupt, is preceded by a more or less long latency period: typically, the turbidimetry follows a sigmoid curve as a function of time. The time required to reach 50% of the maximum turbidimetry is representative of the "clotting time" of conventional clotting assays.

In practice, 100 µl of factor VIII- or factor IX-depleted plasma are preincubated in a microplate at 25° C., and the reaction is triggered by adding 100 µl of kinetics buffer containing 20 mM $CaCl_2$ and 200 nM of activated factor X derivative. The variation in the absorbance at 405 nm as a function of time is recorded using an MR5000 microplate reader. By plotting the variation in absorbance at 405 nm as a function of time, a curve is obtained which makes it possible, by nonlinear regression, to estimate the clotting time ($V_{50}$) using the "Boltzmann equation 7:

$$A_{405} = A_{min} + (A_{max} - A_{min})/(1 + e^{((V_{50} - t)/slope)})$$  (equation 7)

in which $A_{405}$ represents the absorbance at 405 nm at time t, $A_{min}$ the initial absorbance at 405 nm, and $A_{max}$ the final absorbance at 405 nm (after formation of the clot). The slope is a parameter which takes into account the relatively brief nature of the ascending phase in the formation of the clot (the slope increases as the latency period decreases).

The results obtained are summarized in Table XI.

The clotting time (in minutes) of a factor VIII-depleted (−factor VIII) or factor IX-depleted (−factor IX) plasma after addition of the activated form of one of the factor X derivatives is indicated, as is the standard error (expressed as a percentage of the value obtained). Beyond 50 minutes, the value for the clotting time is no longer reliable (>50)

TABLE XI

| Derivative | Clotting time (minutes) | |
| --- | --- | --- |
| | −factor VIII | −factor IX |
| GD-FX | 10.5 (±1%) | 6.5 (±3%) |
| GDX-IVG | 12.6 (±3%) | 6.7 (±1%) |
| GDX-IFG | >50 | 22.9 (±1%) |
| GDX-AVG | 10.9 (±3%) | 7.4 (±3%) |
| GDX-IFR | >50 | >50 |
| GDX-SVG | >50 | >50 |
| GDX-SFR | >50 | >50 |

The activated form of the GD-FX derivative and that of the GDX-IVG derivative have a marked procoagulant effect.

In addition, the potential of the activated form of the GDX-AVG derivative is confirmed: in factor VIII- or factor IX-depleted plasma, this derivative shortens the clotting time as much as the activated form of the GD-FX derivative. The same is not true for the activated form of the GDX-IFG derivative: its procoagulant activity in factor IX-depleted plasma is detectable, but this derivative remains incapable of inducing the formation of a clot in less than 50 minutes in a factor VIII-depleted plasma. The activated forms of the factor X derivatives lacking detectable catalytic activity (GDX-SFR, GDX-SVG and GDX-IFR) have no detectable procoagulant activity.

Procoagulant Effect of the GDX-AVG Derivative (not Activated):

Without tissue factor, there is no clot formation, whether or not the plasma is that of a haemophiliac: the clotting cascade is not initiated. A normal plasma clots, on the other hand, very rapidly after the addition of tissue factor; that of a haemophiliac also eventually clots, because the extrinsic coagulation complex (formed between the tissue factor and factor VIIa) activates factor X, which, within the prothrombinase complex (formed with activated factor V) activates prothrombin to thrombin, which eventually cleaves sufficient fibrinogen to form a clot. The reaction is much slower because there is no amplification involving the tenase complex. The presence of a thrombin-activatable factor X should re-establish an amplification of thrombin generation: two activators would be available: the complex of tissue factor with factor VIIa as previously, but also the thrombin. As the thrombin concentration increases, more and more factor X derivatives are activated, which generate more thrombin, hence the amplification.

A factor X derivative lacking Gla domain does not really make it possible to test its anti-haemophilic potential since its procoagulant action is, in any case, limited. It is, however, possible to verify whether, in the presence of such a derivative, an amplification of thrombin formation takes place after addition of tissue factor.

The method used to detect the procoagulant effect of the factor X derivatives (not activated) is very similar to that described for detecting the activity of their activated forms. The main difference is that the reaction is initiated by adding a mixture of tissue factor and phospholipids (besides the fact that these derivatives are not pre-activated). As for the study of the activated forms, the reaction is carried out in a microplate at 25° C., and the clot formation is followed by turbidimetry, recording the optical density at 405 nm as a function of time. It is the ability of the factor X derivatives to shorten the clotting time of a factor VIII- or factor IX-depleted plasma which is studied.

In practice, the factor X derivative (0.5 μM) is added to 100 μl of factor VIII- or factor IX-depleted plasma, and the reaction is triggered by adding 100 μl of kinetics buffer containing 20 mM $CaCl_2$ and 2 pM of recombinant tissue factor mixed with phospholipids (INNOVIN, DADE BEHRING, La Défense, France). The variation in absorbance at 405 nm as a function of time is recorded using an MR5000 microplate reader, and the time required to reach half the maximum turbidimetry is estimated by non-linear regression using equation 7 as described above for studying the procoagulant activity of the activated forms of the factor X derivatives.

Figure 4:
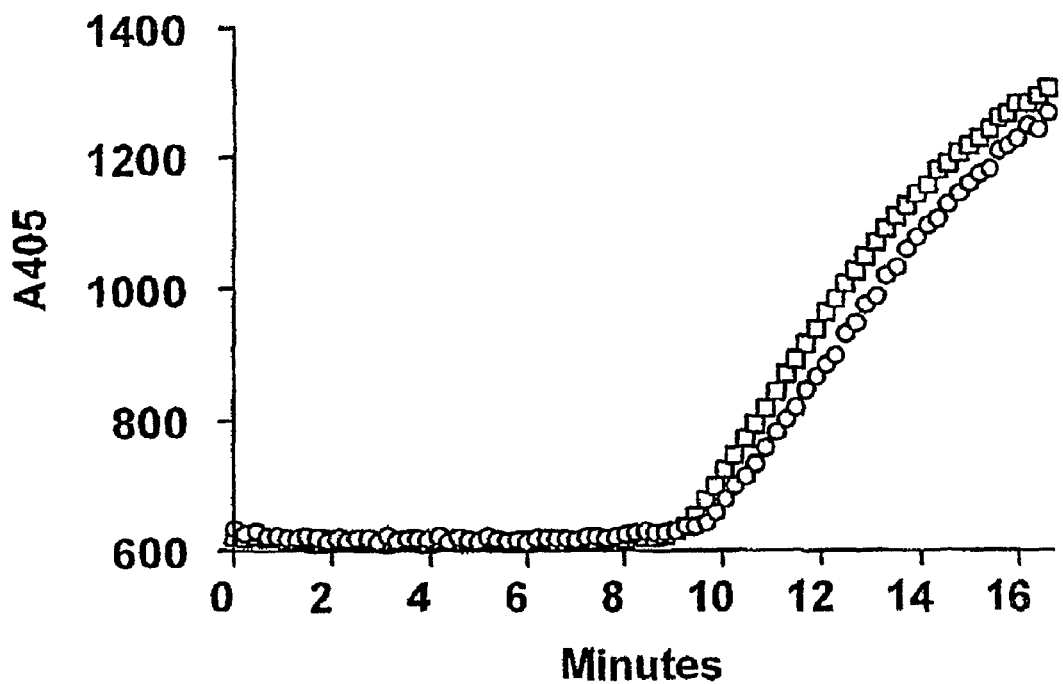
FIG. 4 illustrates the results obtained when the GDX-AVG derivative is added to factor VIII- or factor IX-depleted plasma and the reaction is triggered by adding kinetics buffer.
Figure 4:
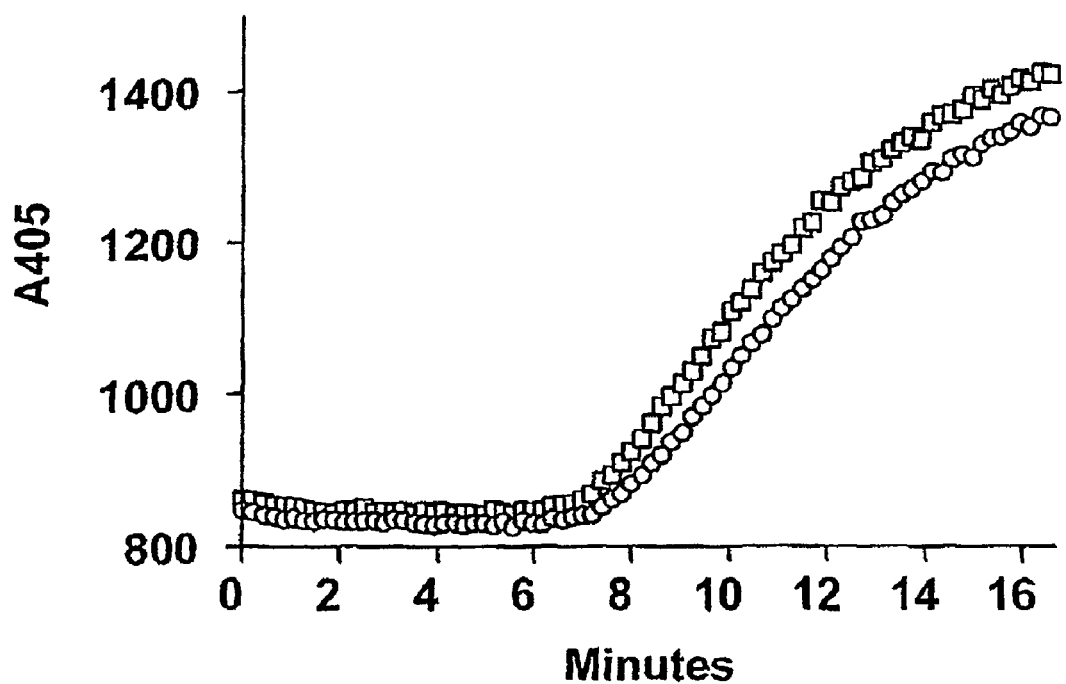

The results obtained with the GDX-AVG derivative (zymogen) are given in FIG. 4, which compares the procoagulant effect of this derivative (○) (not activated) with the GD-FX derivative (□) (not activated) in factor VIII-depleted (4A) or factor IX-depleted (4B) plasma. In the presence of the GDX-AVG derivative, the clotting time is shorter than in the presence of the GD-FX derivative (both in factor VIII-depleted plasma and in factor IX-depleted plasma). The zymogen form of the GDX-AVG derivative therefore clearly has a procoagulant action, despite the absence of Gla domain and its decreased catalytic activity compared to its non-mutated homologue. The fact that the GDX-AVG derivative is more active than the GD-FX derivative suggests that an amplification of thrombin generation has indeed taken place in the presence of GDX-AVG. In fact, compared to the GD-FX derivative, the GDX-AVG derivative is 13 times less active within the prothrombinase complex, where it is at least twice as active in plasma from a haemophiliac: there is therefore production of at least 26 times more activated form of the GDX-AVG derivative during the clot formation.

The invention claimed is:

1. An enhanced human factor X analogue, wherein the sequence Leu-Thr-Arg-Ile-Val-Gly (SEQ ID NO: 1) of the activation site of native factor X is replaced with the sequence Val-Pro-Arg-Ala-Val-Gly (SEQ ID NO: 9).

2. A method of treating coagulopathy resulting from a deficiency in factor VIII, in factor IX or in factor XI in a subject in need thereof comprising administering to said subject a procoagulant medicinal product comprising a human factor X analogue according to claim 1.

3. The method according to claim 2, wherein said coagulopathy is haemophilia type A or haemophilia type B.

4. A human factor Xa analogue which can be obtained by cleavage of a factor X analogue according to claim 1, by thrombin.

5. A nucleic acid molecule encoding a human factor X analogue according to claim 1.

6. A recombinant vector, comprising a nucleic acid molecule according to claim 5.

7. An isolated host cell genetically transformed with a nucleic acid molecule according to claim 5.

8. A procoagulant medicinal product comprising a human factor X analogue according to claim 1.

* * * * *

SEQUENCE LISTING

<160> NUMBER OF SEQ ID NOS: 31

<210> SEQ ID NO 1
<211> LENGTH: 6
<212> TYPE: PRT
<213> ORGANISM: Artificial sequence

```
<220> FEATURE:
<223> OTHER INFORMATION: Factor X activating site

<400> SEQUENCE: 1

Leu Thr Arg Ile Val Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic Peptide

<400> SEQUENCE: 2

Met Pro Arg Ser Phe Arg
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic Peptide

<400> SEQUENCE: 3

Val Pro Arg Ser Phe Arg
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic Peptide

<400> SEQUENCE: 4

Thr Arg Arg Ser Val Gly
1               5

<210> SEQ ID NO 5
<211> LENGTH: 11
<212> TYPE: PRT
<213> ORGANISM: Artificial sequence
<220> FEATURE:
<223> OTHER INFORMATION: Synthetic Peptide

<400> SEQUENCE: 5

Glu Gln Lys Leu Ile Ser Glu Glu Asp Leu Asn
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthetic Peptide

<400> SEQUENCE: 6

Glu Asp Gln Val Asp Pro Arg Leu Ile Asp Gly Lys
1               5                   10

<210> SEQ ID NO 7
<211> LENGTH: 6
<212> TYPE: PRT
<213> ORGANISM: Artificial sequence
<220> FEATURE:
<223> OTHER INFORMATION: Variant of Factor X activating site
```

```
<400> SEQUENCE: 7

Val Pro Arg Ile Val Gly
1               5

<210> SEQ ID NO 8
<211> LENGTH: 6
<212> TYPE: PRT
<213> ORGANISM: Artificial sequence
<220> FEATURE:
<223> OTHER INFORMATION: Variant of Factor X activating site

<400> SEQUENCE: 8

Val Pro Arg Ile Phe Gly
1               5

<210> SEQ ID NO 9
<211> LENGTH: 6
<212> TYPE: PRT
<213> ORGANISM: Artificial sequence
<220> FEATURE:
<223> OTHER INFORMATION: Variant of Factor X activating site

<400> SEQUENCE: 9

Val Pro Arg Ala Val Gly
1               5

<210> SEQ ID NO 10
<211> LENGTH: 6
<212> TYPE: PRT
<213> ORGANISM: Artificial sequence
<220> FEATURE:
<223> OTHER INFORMATION: Variant of Factor X activating site

<400> SEQUENCE: 10

Val Pro Arg Ile Phe Arg
1               5

<210> SEQ ID NO 11
<211> LENGTH: 6
<212> TYPE: PRT
<213> ORGANISM: Artificial sequence
<220> FEATURE:
<223> OTHER INFORMATION: Variant of Factor X activating site

<400> SEQUENCE: 11

Val Pro Arg Ser Val Gly
1               5

<210> SEQ ID NO 12
<211> LENGTH: 6
<212> TYPE: PRT
<213> ORGANISM: Artificial sequence
<220> FEATURE:
<223> OTHER INFORMATION: Variant of Factor X activating site

<400> SEQUENCE: 12

Val Pro Arg Ser Phe Arg
1               5

<210> SEQ ID NO 13
<211> LENGTH: 30
<212> TYPE: DNA
<213> ORGANISM: Artificial sequence
<220> FEATURE:
<223> OTHER INFORMATION: PCR primer

<400> SEQUENCE: 13
```

```
acgcggatcc gcgatggggc gcccactgca                                    30
```

<210> SEQ ID NO 14
<211> LENGTH: 68
<212> TYPE: DNA
<213> ORGANISM: Artificial sequence
<220> FEATURE:
<223> OTHER INFORMATION: PCR primer

<400> SEQUENCE: 14

```
tcccccgggg gatcagttca ggtcttcctc gctgatcagc ttctgctcct ttaatggaga   60
ggacgtta                                                            68
```

<210> SEQ ID NO 15
<211> LENGTH: 21
<212> TYPE: DNA
<213> ORGANISM: Artificial sequence
<220> FEATURE:
<223> OTHER INFORMATION: PCR primer

<400> SEQUENCE: 15

```
tatgcgtggg ctggagcaac c                                             21
```

<210> SEQ ID NO 16
<211> LENGTH: 22
<212> TYPE: DNA
<213> ORGANISM: Artificial sequence
<220> FEATURE:
<223> OTHER INFORMATION: PCR primer

<400> SEQUENCE: 16

```
ttattaggac aaggctggtg gg                                            22
```

<210> SEQ ID NO 17
<211> LENGTH: 21
<212> TYPE: DNA
<213> ORGANISM: Artificial sequence
<220> FEATURE:
<223> OTHER INFORMATION: PCR primer

<400> SEQUENCE: 17

```
cttcccatca atgagccgcg g                                             21
```

<210> SEQ ID NO 18
<211> LENGTH: 42
<212> TYPE: DNA
<213> ORGANISM: Artificial sequence
<220> FEATURE:
<223> OTHER INFORMATION: PCR primer

<400> SEQUENCE: 18

```
ccgcggctca ttgatgggaa ggatggcgac cagtgtgaga cc                      42
```

<210> SEQ ID NO 19
<211> LENGTH: 48
<212> TYPE: DNA
<213> ORGANISM: Artificial sequence
<220> FEATURE:
<223> OTHER INFORMATION: PCR primer

<400> SEQUENCE: 19

```
aggggcgaca acaacgtgcc taggatcgtg ggcggccagg aatgcaag                 48
```

<210> SEQ ID NO 20
<211> LENGTH: 48

```
<212> TYPE: DNA
<213> ORGANISM: Artificial sequence
<220> FEATURE:
<223> OTHER INFORMATION: PCR primer

<400> SEQUENCE: 20
cttgcattcc tggccgccca cgatcctagg cacgttgttg tcgcccct            48

<210> SEQ ID NO 21
<211> LENGTH: 48
<212> TYPE: DNA
<213> ORGANISM: Artificial sequence
<220> FEATURE:
<223> OTHER INFORMATION: PCR primer

<400> SEQUENCE: 21
aggggcgaca caacgtgcc taggatcttc ggcggccagg aatgcaag              48

<210> SEQ ID NO 22
<211> LENGTH: 48
<212> TYPE: DNA
<213> ORGANISM: Artificial sequence
<220> FEATURE:
<223> OTHER INFORMATION: PCR primer

<400> SEQUENCE: 22
cttgcattcc tggccgccga agatcctagg cacgttgttg tcgccct             48

<210> SEQ ID NO 23
<211> LENGTH: 48
<212> TYPE: DNA
<213> ORGANISM: Artificial sequence
<220> FEATURE:
<223> OTHER INFORMATION: PCR primer

<400> SEQUENCE: 23
aggggcgaca caacgtgcc taggatcttc aggggccagg aatgcaag              48

<210> SEQ ID NO 24
<211> LENGTH: 48
<212> TYPE: DNA
<213> ORGANISM: Artificial sequence
<220> FEATURE:
<223> OTHER INFORMATION: PCR primer

<400> SEQUENCE: 24
cttgcattcc tggcccctga agatcctagg cacgttgttg tcgccct             48

<210> SEQ ID NO 25
<211> LENGTH: 48
<212> TYPE: DNA
<213> ORGANISM: Artificial sequence
<220> FEATURE:
<223> OTHER INFORMATION: PCR primer

<400> SEQUENCE: 25
aggggcgaca caacgtgcc taggagcttc aggggccagg aatgcaag              48

<210> SEQ ID NO 26
<211> LENGTH: 48
<212> TYPE: DNA
<213> ORGANISM: Artificial sequence
<220> FEATURE:
<223> OTHER INFORMATION: PCR primer

<400> SEQUENCE: 26
cttgcattcc tggcccctga agctcctagg cacgttgttg tcgccct             48
```

```
<210> SEQ ID NO 27
<211> LENGTH: 29
<212> TYPE: DNA
<213> ORGANISM: Artificial sequence
<220> FEATURE:
<223> OTHER INFORMATION: PCR primer

<400> SEQUENCE: 27
caacgtgcct aggagcgtgg gcggccagg                                   29

<210> SEQ ID NO 28
<211> LENGTH: 29
<212> TYPE: DNA
<213> ORGANISM: Artificial sequence
<220> FEATURE:
<223> OTHER INFORMATION: PCR primer

<400> SEQUENCE: 28
cctggccgcc cacgctccta ggcacgttg                                   29

<210> SEQ ID NO 29
<211> LENGTH: 55
<212> TYPE: DNA
<213> ORGANISM: Artificial sequence
<220> FEATURE:
<223> OTHER INFORMATION: PCR primer

<400> SEQUENCE: 29
cctgagaggg gcgacaacaa cgtgcctagg gccgtgggcg gccaggaatg caagg      55

<210> SEQ ID NO 30
<211> LENGTH: 55
<212> TYPE: DNA
<213> ORGANISM: Artificial sequence
<220> FEATURE:
<223> OTHER INFORMATION: PCR primer

<400> SEQUENCE: 30
ccttgcattc ctggccgccc acggccctag gcacgttgtt gtcgccctc tcagg       55

<210> SEQ ID NO 31
<211> LENGTH: 6
<212> TYPE: PRT
<213> ORGANISM: Artificial sequence
<220> FEATURE:
<223> OTHER INFORMATION: Variants of Factor X activating site
<220> FEATURE:
<221> NAME/KEY: MISC_FEATURE
<222> LOCATION: (1)..(1)
<223> OTHER INFORMATION: Xaa= Ala, Cys, Phe, Gly, His, Ile, Lys, Leu,
      Met, Asn, Gln, Arg, Ser, Thr, Val, Trp ou Tyr
<220> FEATURE:
<221> NAME/KEY: MISC_FEATURE
<222> LOCATION: (5)..(5)
<223> OTHER INFORMATION: Xaa= Val, Ile, Leu ou Phe
<220> FEATURE:
<221> NAME/KEY: MISC_FEATURE
<222> LOCATION: (6)..(6)
<223> OTHER INFORMATION: Xaa= Gly, Asn ou His

<400> SEQUENCE: 31

Xaa Pro Arg Ala Xaa Xaa
1               5
```